United States Patent
Witzel et al.

(10) Patent No.: US 8,328,798 B2
(45) Date of Patent: Dec. 11, 2012

(54) METHOD FOR TREATING AND REPAIRING MITRAL VALVE ANNULUS

(75) Inventors: Thomas Witzel, Laguna Niguel, CA (US); Wallace N Hauck, Irvine, CA (US); John A. Osth, Laguna Hills, CA (US); Hosheng Tu, Newport Beach, CA (US)

(73) Assignee: Quantumcor, Inc, Laguna Niguel, CA (US)

( * ) Notice: Subject to any disclaimer, the term of this patent is extended or adjusted under 35 U.S.C. 154(b) by 560 days.

(21) Appl. No.: 11/749,005

(22) Filed: May 15, 2007

(65) Prior Publication Data

US 2008/0091191 A1    Apr. 17, 2008

Related U.S. Application Data

(63) Continuation of application No. 10/423,999, filed on Apr. 26, 2003, now Pat. No. 7,229,469, and a continuation-in-part of application No. 10/292,824, filed on Nov. 12, 2002, now abandoned, which is a continuation-in-part of application No. 10/101,230, filed on Mar. 19, 2002, now Pat. No. 6,485,489, which is a continuation-in-part of application No. 10/083,264, filed on Oct. 22, 2001, now abandoned, which is a continuation-in-part of application No. 09/410,902, filed on Oct. 2, 1999, now Pat. No. 6,306,133.

(60) Provisional application No. 60/383,725, filed on May 28, 2002.

(51) Int. Cl.
*A61B 18/12* (2006.01)

(52) U.S. Cl. ............................................ 606/41; 606/33

(58) Field of Classification Search ............... 606/41–52
See application file for complete search history.

(56) References Cited

U.S. PATENT DOCUMENTS

| | | | |
|---|---|---|---|
| 3,656,185 A | 4/1972 | Carpentier |
| 4,164,046 A | 8/1979 | Cooley |
| 4,215,015 A | 7/1980 | Tu |
| 4,238,243 A | 12/1980 | Tu et al. |
| 4,239,615 A | 12/1980 | Tu |
| 4,250,059 A | 2/1981 | Tu |
| 4,261,861 A | 4/1981 | Tu et al. |
| 4,263,174 A | 4/1981 | Tu et al. |
| 4,264,473 A | 4/1981 | Tu et al. |
| 4,280,897 A | 7/1981 | Shah et al. |
| 4,291,186 A | 9/1981 | Tu |
| 4,295,955 A | 10/1981 | Tu |

(Continued)

FOREIGN PATENT DOCUMENTS

WO    WO 00/04130    8/2000

(Continued)

*Primary Examiner* — Michael Peffley
*Assistant Examiner* — Daniel Fowler
(74) *Attorney, Agent, or Firm* — Cotman IP Law Group, PLC

(57) ABSTRACT

A catheter system for repairing an annular organ structure of a patient, comprising: intimately contacting the annular organ structure by a tissue-contactor member having energy-delivering elements; and delivering tissue-shrinkable energy at the annular organ structure through the elements, wherein the tissue-shrinkable energy is applied at a distance wirelessly from the elements sufficient to shrink and tighten the organ structure. Tissue-shrinkable energy is infrared energy, ultrasound energy, focused ultrasound energy, ultrasound energy, radiofrequency energy, microwave energy, electromagnetic energy, laser energy, or a combination thereof.

12 Claims, 22 Drawing Sheets

U.S. PATENT DOCUMENTS

| | | | |
|---|---|---|---|
| 4,299,688 A | 11/1981 | Tu et al. | |
| 4,299,733 A | 11/1981 | Tu | |
| 4,300,012 A | 11/1981 | Tu et al. | |
| 4,305,845 A | 12/1981 | Tu | |
| 4,312,743 A | 1/1982 | Tu et al. | |
| 4,312,744 A | 1/1982 | Tu et al. | |
| 4,316,819 A | 2/1982 | Tu et al. | |
| 4,333,821 A | 6/1982 | Tu | |
| 4,337,145 A | 6/1982 | Tu | |
| 4,343,723 A | 8/1982 | Rogers et al. | |
| 4,345,946 A | 8/1982 | Tu et al. | |
| 4,348,272 A | 9/1982 | Tu | |
| 4,364,847 A | 12/1982 | Tu | |
| 4,658,828 A | 4/1987 | Dory | |
| 4,816,339 A | 3/1989 | Tu et al. | |
| 4,882,113 A | 11/1989 | Tu et al. | |
| 4,951,653 A | 8/1990 | Fry et al. | |
| RE33,590 E | 5/1991 | Dory | |
| 5,024,671 A | 6/1991 | Tu et al. | |
| 5,054,470 A | 10/1991 | Fry et al. | |
| 5,061,276 A | 10/1991 | Tu et al. | |
| 5,071,609 A | 12/1991 | Tu et al. | |
| 5,080,101 A | 1/1992 | Dory | |
| 5,080,102 A | 1/1992 | Dory | |
| 5,100,429 A | 3/1992 | Sinofsky et al. | |
| 5,143,074 A | 9/1992 | Dory | |
| 5,150,711 A | 9/1992 | Dory | |
| 5,150,712 A | 9/1992 | Dory | |
| 5,295,484 A | 3/1994 | Marcus et al. | |
| 5,341,807 A * | 8/1994 | Nardella | 600/381 |
| 5,354,258 A | 10/1994 | Dory | |
| 5,376,110 A | 12/1994 | Tu et al. | |
| 5,391,197 A | 2/1995 | Burgette et al. | |
| 5,431,621 A | 7/1995 | Dory | |
| 5,431,649 A * | 7/1995 | Mulier et al. | 606/41 |
| 5,456,662 A | 10/1995 | Edwards et al. | |
| 5,492,126 A | 2/1996 | Hennige et al. | |
| 5,501,655 A | 3/1996 | Rolt et al. | |
| 5,546,954 A | 8/1996 | Yamada | |
| 5,549,666 A | 8/1996 | Hata et al. | |
| 5,609,934 A | 3/1997 | Fay | |
| 5,674,279 A | 10/1997 | Wright et al. | |
| 5,676,692 A | 10/1997 | Sanghvi et al. | |
| 5,762,066 A | 6/1998 | Law et al. | |
| 5,769,780 A | 6/1998 | Hata et al. | |
| 5,779,715 A | 7/1998 | Tu | |
| 5,792,140 A | 8/1998 | Tu et al. | |
| 5,792,900 A | 8/1998 | Lee et al. | |
| 5,843,020 A | 12/1998 | Tu et al. | |
| 5,843,152 A | 12/1998 | Tu et al. | |
| 5,868,741 A | 2/1999 | Chia et al. | |
| 5,873,845 A | 2/1999 | Cline et al. | |
| 5,876,340 A | 3/1999 | Tu et al. | |
| 5,876,399 A | 3/1999 | Chia et al. | |
| 5,891,027 A | 4/1999 | Tu et al. | |
| 5,891,137 A | 4/1999 | Chia et al. | |
| 5,891,138 A | 4/1999 | Tu et al. | |
| 5,893,884 A | 4/1999 | Tu | |
| 5,895,356 A | 4/1999 | Andrus et al. | |
| 5,897,554 A | 4/1999 | Chia et al. | |
| 5,913,856 A | 6/1999 | Chia et al. | |
| 5,921,954 A * | 7/1999 | Mohr et al. | 604/508 |
| 5,928,224 A * | 7/1999 | Laufer | 606/27 |
| 5,938,658 A | 8/1999 | Tu | |
| 5,938,659 A | 8/1999 | Tu et al. | |
| 5,941,845 A | 8/1999 | Tu et al. | |
| 5,947,977 A | 9/1999 | Slepian et al. | |
| 5,948,009 A | 9/1999 | Tu | |
| 5,951,471 A | 9/1999 | De La Rama et al. | |
| 5,954,649 A | 9/1999 | Chia et al. | |
| 5,957,862 A | 9/1999 | Lu et al. | |
| 5,968,005 A | 10/1999 | Tu | |
| 5,971,968 A | 10/1999 | Tu et al. | |
| 5,980,515 A | 11/1999 | Tu et al. | |
| 5,980,563 A | 11/1999 | Tu et al. | |
| 5,989,248 A | 11/1999 | Tu et al. | |
| 5,989,284 A | 11/1999 | Laufer | |
| 5,992,418 A | 11/1999 | De La Rama et al. | |
| 5,997,534 A | 12/1999 | Tu et al. | |
| 6,001,095 A | 12/1999 | De La Rama et al. | |
| 6,006,123 A | 12/1999 | Nguyen et al. | |
| 6,016,437 A | 1/2000 | Tu et al. | |
| 6,017,324 A | 1/2000 | Tu et al. | |
| 6,024,742 A | 2/2000 | Tu et al. | |
| 6,033,402 A | 3/2000 | Tu et al. | |
| 6,033,403 A | 3/2000 | Tu et al. | |
| 6,036,689 A | 3/2000 | Tu et al. | |
| 6,050,993 A | 4/2000 | Tu et al. | |
| 6,053,913 A | 4/2000 | Tu et al. | |
| 6,061,277 A | 5/2000 | Lines | |
| 6,068,645 A | 5/2000 | Tu | |
| 6,071,281 A * | 6/2000 | Burnside et al. | 606/41 |
| 6,077,298 A | 6/2000 | Tu et al. | |
| 6,079,414 A | 6/2000 | Roth | |
| 6,083,219 A | 7/2000 | Laufer | |
| 6,090,134 A | 7/2000 | Tu et al. | |
| 6,096,033 A | 8/2000 | Tu et al. | |
| 6,102,908 A | 8/2000 | Tu et al. | |
| 6,104,952 A | 8/2000 | Tu et al. | |
| 6,113,593 A | 9/2000 | Tu et al. | |
| 6,123,703 A | 9/2000 | Tu et al. | |
| 6,123,718 A | 9/2000 | Tu et al. | |
| 6,129,725 A | 10/2000 | Tu et al. | |
| 6,135,997 A | 10/2000 | Laufer et al. | |
| 6,149,647 A | 11/2000 | Tu et al. | |
| 6,156,033 A | 12/2000 | Tu | |
| 6,161,548 A | 12/2000 | Tu | |
| 6,165,206 A | 12/2000 | Tu | |
| 6,179,789 B1 | 1/2001 | Tu et al. | |
| 6,197,022 B1 * | 3/2001 | Baker | 606/33 |
| 6,200,315 B1 * | 3/2001 | Gaiser et al. | 606/41 |
| 6,206,831 B1 | 3/2001 | Suorsa et al. | |
| 6,206,842 B1 | 3/2001 | Tu et al. | |
| 6,217,576 B1 | 4/2001 | Tu et al. | |
| 6,221,070 B1 | 4/2001 | Tu et al. | |
| 6,226,554 B1 | 5/2001 | Tu et al. | |
| 6,228,109 B1 | 5/2001 | Tu et al. | |
| 6,231,570 B1 | 5/2001 | Tu et al. | |
| 6,233,477 B1 | 5/2001 | Chia et al. | |
| 6,235,024 B1 | 5/2001 | Tu et al. | |
| 6,238,390 B1 | 5/2001 | Tu et al. | |
| 6,238,421 B1 * | 5/2001 | Gunther et al. | 607/13 |
| 6,241,692 B1 | 6/2001 | Tu et al. | |
| 6,241,726 B1 | 6/2001 | Chia et al. | |
| 6,241,727 B1 | 6/2001 | Tu et al. | |
| 6,245,067 B1 | 6/2001 | Tu et al. | |
| 6,246,899 B1 | 6/2001 | Chia et al. | |
| 6,246,914 B1 | 6/2001 | De La Rama et al. | |
| 6,258,087 B1 | 7/2001 | Edwards et al. | |
| 6,258,122 B1 | 7/2001 | Tweden et al. | |
| 6,259,941 B1 | 7/2001 | Chia et al. | |
| 6,267,781 B1 | 7/2001 | Tu | |
| 6,283,962 B1 | 9/2001 | Tu et al. | |
| 6,284,284 B1 | 9/2001 | Naughton | |
| 6,290,697 B1 | 9/2001 | Tu et al. | |
| 6,303,765 B1 | 10/2001 | Bandman et al. | |
| 6,306,133 B1 | 10/2001 | Tu et al. | |
| 6,308,090 B1 | 10/2001 | Tu et al. | |
| 6,319,251 B1 | 11/2001 | Tu et al. | |
| 6,322,583 B1 | 11/2001 | Tu et al. | |
| 6,346,105 B1 | 2/2002 | Tu et al. | |
| 6,355,030 B1 * | 3/2002 | Aldrich et al. | 606/28 |
| 6,361,531 B1 | 3/2002 | Hissong | |
| 6,385,472 B1 | 5/2002 | Hall et al. | |
| 6,402,781 B1 | 6/2002 | Langberg et al. | |
| 6,406,493 B1 | 6/2002 | Tu et al. | |
| 6,423,023 B1 | 7/2002 | Chang et al. | |
| 6,423,056 B1 * | 7/2002 | Ishikawa et al. | 606/28 |
| 6,451,011 B2 | 9/2002 | Tu | |
| 6,451,044 B1 | 9/2002 | Naghaus et al. | |
| 6,464,707 B1 | 10/2002 | Bjerken | |
| 6,485,489 B2 | 11/2002 | Teirstein et al. | |
| 6,506,398 B1 | 1/2003 | Tu et al. | |
| 6,551,312 B2 | 4/2003 | Zhang et al. | |
| 6,569,163 B2 | 5/2003 | Hata et al. | |
| 6,575,971 B2 | 6/2003 | Hauck et al. | |
| 6,595,934 B1 * | 7/2003 | Hissong et al. | 601/3 |

| | | |
|---|---|---|
| 6,624,138 B1 | 9/2003 | Sung et al. |
| 6,626,899 B2 | 9/2003 | Houser et al. |
| 6,652,517 B1 * | 11/2003 | Hall et al. .................. 606/41 |
| 6,666,841 B2 | 12/2003 | Gharib et al. |
| 6,668,198 B2 | 12/2003 | Swanson et al. |
| 6,682,558 B2 | 1/2004 | Tu et al. |
| 6,685,702 B2 | 2/2004 | Quijano et al. |
| 6,736,791 B1 | 5/2004 | Tu et al. |
| 6,805,711 B2 | 10/2004 | Quijano et al. |
| 6,807,444 B2 | 10/2004 | Tu et al. |
| 6,830,585 B1 | 12/2004 | Artof et al. |
| 6,830,586 B2 | 12/2004 | Quijano et al. |
| 6,832,111 B2 | 12/2004 | Tu et al. |
| 6,875,231 B2 | 4/2005 | Anduiza et al. |
| 6,926,715 B1 | 8/2005 | Hauck et al. |
| 6,939,359 B2 | 9/2005 | Tu et al. |
| 6,949,518 B1 | 9/2005 | Chu et al. |
| 6,960,178 B2 | 11/2005 | Chang et al. |
| 6,969,367 B2 | 11/2005 | Tu et al. |
| 6,974,464 B2 | 12/2005 | Quijano et al. |
| 6,981,958 B1 | 1/2006 | Gharib et al. |
| 6,998,418 B1 | 2/2006 | Sung et al. |
| 7,004,911 B1 | 2/2006 | Tu et al. |
| 7,029,675 B1 | 4/2006 | Lin et al. |
| 7,041,132 B2 | 5/2006 | Quijano et al. |
| 7,060,684 B1 | 6/2006 | Quijano et al. |
| 7,094,225 B2 | 8/2006 | Tu et al. |
| 7,101,857 B2 | 9/2006 | Sung et al. |
| 7,135,009 B2 | 11/2006 | Tu et al. |
| 7,153,299 B1 | 12/2006 | Tu et al. |
| 7,163,543 B2 | 1/2007 | Smedley et al. |
| 7,186,232 B1 | 3/2007 | Smedley et al. |
| 7,229,469 B1 | 6/2007 | Witzel et al. |
| 2001/0007940 A1 * | 7/2001 | Tu et al. ................. 606/41 |
| 2001/0034519 A1 * | 10/2001 | Goble et al. ............. 606/41 |
| 2002/0035361 A1 | 3/2002 | Houser et al. |
| 2002/0049439 A1 * | 4/2002 | Mulier et al. ............. 606/41 |
| 2002/0082594 A1 * | 6/2002 | Hata et al. ............... 606/41 |
| 2002/0115994 A1 * | 8/2002 | Teirstein et al. ......... 606/41 |
| 2005/0240249 A1 | 10/2005 | Tu et al. |

FOREIGN PATENT DOCUMENTS

WO    WO 01/50930    7/2001

* cited by examiner

METHOD FOR TREATING AND REPAIRING MITRAL VALVE ANNULUS

This application is a continuation of application Ser. No. 10/423,999, filed Apr. 26, 2003, now Pat. No. 7,229,469, which claims the benefit of U.S. provisional application Ser. No. 60/383,725 filed May 28, 2002, wherein application Ser. No. 10/423,999 is a continuation-in-part of application Ser. No. 10/292,824, filed Nov. 11, 2002, now abandoned, which is a continuation-in-part of application Ser. No. 10/101,230, filed Mar. 19, 2002, now U.S. Pat. No. 6,485,489, which is a continuation-in-part of application Ser. No. 10/083,264, filed Oct. 22, 2001, now abandoned, which is a continuation-in-part of application Ser. No. 09/410,902 filed Oct. 2, 1999, now U.S. Pat. No. 6,306,133, all of which are hereby incorporated herein by reference.

BACKGROUND OF THE INVENTION

Over 12 million people around the world suffer from Congestive Heart Failure (CHF). This is a family of related conditions defined by the failure of the heart to pump blood efficiently resulting in congestion (or backing up of the blood) in the lungs or peripheral circulation. CHF can ultimately lead to end-organ failure, which contributes to death of the patient. The heart muscle of the CHF patient may be altered with the chambers dilated and the heart walls thickened or thinned. CHF can result from several conditions, including infections of the heart muscle or valve, physical damage to the valve or by damaged muscle caused by infarction (heart attack).

CHF is the fastest growing cardiovascular disease with over 1 million new cases occurring each year. Conservative estimates suggest that the prevalence of CHF will more than double by 2007. If untreated, CHF may result in severe lifestyle restrictions and ultimately death. One of the causes of CHF and a very common contributor to the harmful effects of CHF is a leaky mitral heart valve. The mitral valve is located in the center of the heart between the two left or major heart chambers and plays an important role in maintaining forward flow of blood. The medical term for this leaky condition is "mitral regurgitation" and the condition affects well over one million people globally. Mitral regurgitation is also called 'mitral incompetence' or 'mitral insufficiency'.

For general background information, the circulatory system consists of a heart and blood vessels. In its path through the heart, the blood encounters four valves. The valve on the right side that separates the right atrium from the right ventricle has three cusps and is called the tricuspid valve. It closes when the ventricle contracts during a phase known as systole and it opens when the ventricle relaxes, a phase known as diastole.

The pulmonary valve separates the right ventricle from the pulmonary artery. It opens during systole, to allow the blood to be pumped toward the lungs, and it closes during diastole to keep the blood from leaking back into the heart from the pulmonary artery. The pulmonary valve has three cusps, each one resembling a crescent and it is also known as a semi-lunar valve.

The two-cusped mitral valve, so named because of its resemblance to a bishop's mitre, is in the left ventricle and it separates the left atrium from the ventricle. It opens during diastole to allow the blood stored in the atrium to pour into the ventricle, and it closes during systole to prevent blood from leaking back into the atrium. The mitral valve and the tricuspid valve differ significantly in anatomy. The annulus of the mitral valve is somewhat D-shaped whereas the annulus of the tricuspid valve is more nearly circular.

The fourth valve is the aortic valve. It separates the left ventricle from the aorta. It has three semi-lunar cusps and it closely resembles the pulmonary valve. The aortic valve opens during systole allowing a stream of blood to enter the aorta and it closes during diastole to prevent any of the blood from leaking back into the left ventricle.

In a venous circulatory system, a venous valve functions to prevent the venous blood from leaking back into the upstream side so that the venous blood can return to the heart and the lungs for blood oxygenating purposes.

Clinical experience has shown that repair of a valve, either a heart valve or a venous valve, produces better long-term results than does valve replacement. Valve replacement using a tissue valve suffers long-term calcification problems. On the other hand, anticoagulation medicine, such as cumadin, is required for the life of a patient when a mechanical valve is used in valve replacement. The current technology for valve repair or valve replacement requires an expensive open-heart surgery that needs a prolonged period of recovery. A less invasive or catheter-based valve repair technology becomes an unmet clinical challenge.

The effects of valvular dysfunction vary. Mitral regurgitation may have more severe physiological consequences to the patient than does tricuspid valve regurgitation. In patients with valvular insufficiency, it is an increasingly common surgical practice to repair the natural valve, and to attempt to correct the defects. Many of the defects are associated with dilation of the valve annulus. This dilatation not only prevents competence of the valve but also results in distortion of the normal shape of the valve orifice or valve leaflets. Remodeling of the annulus is therefore central to most reconstructive procedures for the mitral valve.

As a part of the valve repair it is either necessary to diminish or constrict the involved segment of the annulus so that the leaflets may coapt correctly on closing, or to stabilize the annulus to prevent post operative dilatation from occurring. The current open-heart approach is by implantation of a prosthetic ring, such as a Cosgrove Ring or a Carpentier Ring, in the supra annular position. The purpose of the ring is to restrict and/or support the annulus to correct and/or prevent valvular insufficiency. In tricuspid valve repair, constriction of the annulus usually takes place in the posterior leaflet segment and in a small portion of the adjacent anterior leaflet.

Various prostheses have been described for use in conjunction with mitral or tricuspid valve repair. The ring developed by Dr. Alain Carpentier (U.S. Pat. No. 3,656,185) is rigid and flat. An open ring valve prosthesis as described in U.S. Pat. No. 4,164,046 comprises a uniquely shaped open ring valve prosthesis having a special velour exterior for effecting mitral and tricuspid annuloplasty. The fully flexible annuloplasty ring could only be shortened in the posterior segment by the placement of plicating sutures. John Wright et al. in U.S. Pat. No. 5,674,279 discloses a suturing ring suitable for use on heart valve prosthetic devices for securing such devices in the heart or other annular tissue. All of the above valve repair or replacement requires an open-heart operation which is costly and exposes a patient to higher risk and longer recovery than a catheter-based, less invasive procedure.

Moderate heat is known to tighten and shrink the collagen tissue as illustrated in U.S. Pat. Nos. 5,456,662 and 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36-44, August 1998). Therefore, it becomes imperative to treat the inner walls of an annular organ structure of a heart valve, a valve leaflet, chordae tendinae, papillary muscles, and the like by shrinking/tightening techniques. The same shrinking/tightening techniques are also applicable to stabilize injected biomaterial to repair the defect annular organ structure, wherein the injectable biomaterial is suitable for penetration and heat initiated shrinking/tightening.

One method of reducing the size of tissues in situ has been used in the treatment of many diseases, or as an adjunct to surgical removal procedures. This method applies appropriate heat to the tissues, and causes them to shrink and tighten. It can be performed in a minimal invasive or percutaneous fashion, which is often less traumatic than surgical procedures and may be the only alternative method, wherein other procedures are unsafe or ineffective. Ablative treatment devices have an advantage because of the use of a therapeutic energy that is rapidly dissipated and reduced to a non-destructive level by conduction and convection, to other natural processes.

Radio frequency (RF) therapeutic protocol has been proven to be highly effective when used by electrophysiologists for the treatment of tachycardia, atrial flutter and atrial fibrillation; by neurosurgeons for the treatment of Parkinson's disease; by otolaryngologist for clearing airway obstruction and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the device to tissue contact site to obtain the desired temperature for treating a tissue or for effecting the desired shrinking of the host collagen or injected bioresorbable material adapted to immobilize the biomaterial in place. Tweden, et al, in U.S. Pat. No. 6,258,122, entire content which are incorporated herein by reference, discloses that a bioresorbable heart valve annuloplasty prosthesis are eventually resorbed by the patient, during which time regenerated tissue replaces the prosthesis Edwards et al in U.S. Pat. No. 6,258,087, entire contents of which are incorporated herein by reference, discloses an expandable electrode assembly comprising a support basket formed from an array of spines for forming lesions to treat dysfunction in sphincters. Electrodes carried by the spines are intended to penetrate the tissue region upon expansion of the basket. However, the assembly disclosed by Edwards et al. does not teach a tissue-contactor member comprising a narrow middle region between an enlarged distal region and an enlarged proximal region suitable for sandwiching and compressing the sphincter for tissue treatment.

Tu in U.S. Pat. No. 6,267,781 teaches an ablation device for treating valvular annulus or valvular organ structure of a patient, comprising a flexible elongate tubular shaft having a deployable spiral wire electrode at its distal end adapted to contact/penetrate the tissue to be treated and to apply high frequency energy to the tissue for therapeutic purposes. Tu et al. in U.S. Pat. No. 6,283,962 discloses a medical ablation for treating valvular annulus wherein an elongate tubular element comprises an electrode disposed at its distal section that is extendible from an opening at one side of the tubular element, the energy generator, and means for generating rotational sweeping force at the distal section of the tubular element to effect the heat treatment and the rotational sweeping massage therapy for target tissues. Both patents, entire contents of which are incorporated herein by reference, teach only the local tissue shrinkage, not for treating simultaneously a substantial portion of the valvular annulus.

U.S. Pat. No. 6,402,781 issued on Jun. 11, 2002, entire contents of which are incorporated herein by reference, discloses a mitral annuloplasty and left ventricle restriction device designed to be transvenously advanced and deployed within the coronary sinus and in some embodiments other coronary veins. The device places tension on adjacent structures, reducing the diameter and/or limiting expansion of the mitral annulus and/or limiting diastolic expansion of the left ventricle.

Hissong in U.S. Pat. No. 6,361,531 issued Mar. 26, 2002, entire contents of which are incorporated herein by reference, discloses focused ultrasound ablation device having malleable handle shafts. A remote energy source, such as ultrasound or microwave energy, can be emitted wirelessly to a focused target tissue located away from the ultrasound device. However, it is not disclosed for focused ultrasound energy for repairing a mitral valve or an atrioventricular valve annulus.

Therefore, there is a clinical need to have a percutaneous, or less invasive catheter or cannula-based approach as well as a surgical hand-held device for repairing an annular organ structure of a heart valve, a valve leaflet, chordae tendinae, papillary muscles, and the tissue defect by using high frequency energy (RF, microwave or ultrasound) for reducing and/or shrinking a tissue mass, with optionally an injected heat shrinkable biomaterial along with the host tissue mass for tightening and stabilizing the dilated tissue adjacent a valvular annulus. There is also a clinical need for an improved apparatus system having capabilities of measuring a contact force at the point of contact with the tissue to be treated, as disclosed by one of inventors in U.S. Pat. No. 6,113,593, entire contents which are incorporated herein by reference.

BRIEF SUMMARY OF THE INVENTION

In general, it is an object of the present invention to provide a medical system and methods for repairing an annular organ structure of a heart valve, an annular organ structure of a venous valve, a valve leaflet, chordae tendinae, papillary muscles, a sphincter, and the like. The system may be deployed into the heart via a catheter percutaneously or via a cannula through a percutaneous intercostal penetration (minimally invasive) or with a surgical hand-held device during an open chest procedure. The system may be deployed into a sphincter via trans thoracic or trans abdominal approaches or via urogenital or gastrointestinal orifices. The system may be deployed into a venous valve using local surgical approaches or by percutaneous access into the venous system. The effective tissue-shrinkable energy may be applied at a distance wirelessly from the target annular organ sufficient to shrink and tighten the target organ structure.

It is another object of the present invention to provide a catheter, cannula or surgical system and methods by using cryoablation energy, radiofrequency energy, or high frequency current for tissue treatment or repairing and causing the tissue to shrink or tighten. The high frequency energy may include radiofrequency, focused ultrasound, infrared, or microwave energy, wherein the high, frequent focused current is applied noninvasively from outside of a body.

It is still another object to provide a catheter-based less invasive system that intimately contacts the tissue of an annulus in order to tighten and stabilize a substantial portion of the dysfunctional annular organ structure simultaneously or sequentially. The step of intimately contacting may be assisted by a needles penetrating system or a suction ports system for anchoring the energy-releasing elements.

It is still another aspect of the present invention to provide a catheter-based less invasive system that transmits an effective amount of the high frequency ultrasound or microwave current energy through a medium tissue onto the target annulus in order to tighten and stabilize a substantial portion of the dysfunctional annular organ structure. In one embodiment, the catheter with a distal ultrasound transducer is placed inside a coronary vein.

It is a general aspect of the present invention to provide a method for repairing a valvular annulus defect comprising locating the valvular annulus defect via a plurality of ultrasound signals emitted from a catheter as auxiliary locating means; and applying remotely effective tissue-shrinkable energy sufficient to treat the valvular annulus by focusing the energy at about the annulus defect.

It is a preferred object to provide a method for repairing a valvular annulus defect comprising injecting a heat shapeable biomaterial formulated for in vivo administration by injection via a delivery system at a site of the valvular annulus defect; and applying heat sufficient to shape the biomaterial and immobilize the biomaterial at about the annulus defect.

It is another preferred object of the present invention to provide a flexible tissue-contactor member located at the distal tip section of a catheter shaft for compressively sandwiching and contacting an inner wall of an annular organ structure, wherein the tissue-contactor member includes an expandable structure having a narrow middle region and enlarged end regions that is generally configured to snugly fit and sandwich the inner wall of an annular organ structure for optimal therapy that is characterized by exerting compression onto the inner wall.

It is another object of the invention to provide a method for repairing a tissue defect comprising: injecting a heat shapeable biomaterial formulated for in vivo administration by injection via a percutaneous delivery system at a site of the tissue defect; and applying heat to the biomaterial and a portion of the tissue defect adapted for shaping the biomaterial, the heat being below a temperature sufficient for effecting crosslinking of the biomaterial and the portion of the tissue defect. In one embodiment, the tissue contact side is provided with a dual ablation capability of RF and ultrasound energy. In another embodiment, the biomaterial acts as an annular support and is biodegradable. Heat applied to the biomaterial will cause shape changes to the host annulus. In yet another embodiment, the heat is provided by RF, ultrasound, microwave, infrared or combination thereof.

It is still another object of the present invention to provide a catheter system and methods for providing high frequency current energy to the tissue needed for treatment at or adjacent to an annular organ structure. In one embodiment, the catheter system is placed remotely from and/or non-contacting with the target tissue. In another embodiment, it is provided a catheter having a working distal end that is covered by a plurality of adjacent filaments which are bound together by suturing, braiding, jacketing or encapsulating to provide a non-skid surface.

In one embodiment, the method for operating a catheter system for repairing a valvular annulus or a valveless annulus comprising compressively sandwiching the annulus by a tissue-contactor member and delivering high frequency energy to the annulus, wherein the tissue-contactor member is configured to have a narrow middle region between an enlarged distal region and an enlarged proximal region adapted for compressively sandwiching the annulus at about the middle region for subsequent tissue treatment.

It is still another object of the present invention to provide a catheter system and methods for providing high frequency current to a restriction device, possibly biodegradable, designed to be transversely advanced and deployed within the cardiac vein via the coronary sinus and in some embodiments other coronary veins. This device, when heated, will place tension on adjacent structures, reducing the diameter and/or limiting the expansion of the mitral annulus and/or diastolic expansion of the left ventricle.

It is another preferred object of the present invention to provide a magnetic system for position the energy producing members of the catheter system and to secure the position once it is in place. One embodiment would consist of a single magnet or a series of magnets embedded in the catheter in or near the energy producing electrode. An opposing catheter with a single magnet or a series of magnets would be placed either in a coronary vein, inside a heart chamber, outside the heart, or outside the body. The two catheters would line magnetically to position the energy producing catheter over or near the annulus and hold it in place.

It is a general aspect of the present invention to provide a method for repairing a valvular annulus defect comprising locating the valvular annulus defect via a plurality of ultrasound signals emitted from a catheter as auxiliary locating means; and applying remotely effective tissue-shrinkable energy sufficient to treat the valvular annulus by focusing the energy at about the annulus defect.

The catheter system of the present invention has several significant advantages over known catheters or ablation techniques for repairing an annular organ structure of a heart valve, a valve leaflet, chordae tendinae, papillary muscles, venous valve, sphincter, and the like. In particular, the ablation catheter of this invention by using high frequency current energy for reducing and/or shrinking a tissue mass may tighten and stabilize the dilated tissue at or adjacent a valvular annulus.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION

The following descriptions of the embodiment of the invention are exemplary, rather than limiting, and many variations and modifications are within the scope of the invention. What is shown in FIGS. 1 to 21 is an embodiment of the present invention to provide a treating system that selectively contacts the tissue of an annulus in order to tighten and stabilize an annular organ structure adapted for repairing an annular organ structure defect of a patient. The system may be deployed via a catheter percutaneously or via a cannula through a percutaneous intercostal penetration or applied directly to the annular organ via open surgical access. The annular organ structure or the annulus to be treated may be selected from the group consisting of a mitral valve, a tricuspid valve, a pulmonary valve, an aortic valve, a venous valve, and a sphincter.

"Sandwich" as a verb is herein meant to place an object between usually two things of another quality or character; particularly intended to mean confining an annulus between two radially enlarged end regions of a tissue-contactor member characterized by certain degrees of compression onto the annulus exerted from the two end regions.

It is one aspect of the invention to provide a method for repairing a valvular annulus defect comprising injecting a heat shapeable or solidifiable biomaterial formulated for in vivo administration by injection via a delivery system at a site of the valvular annulus defect; and applying heat sufficient to shape the biomaterial and immobilize/solidify the biomaterial at about the annulus defect.

Figure 1:
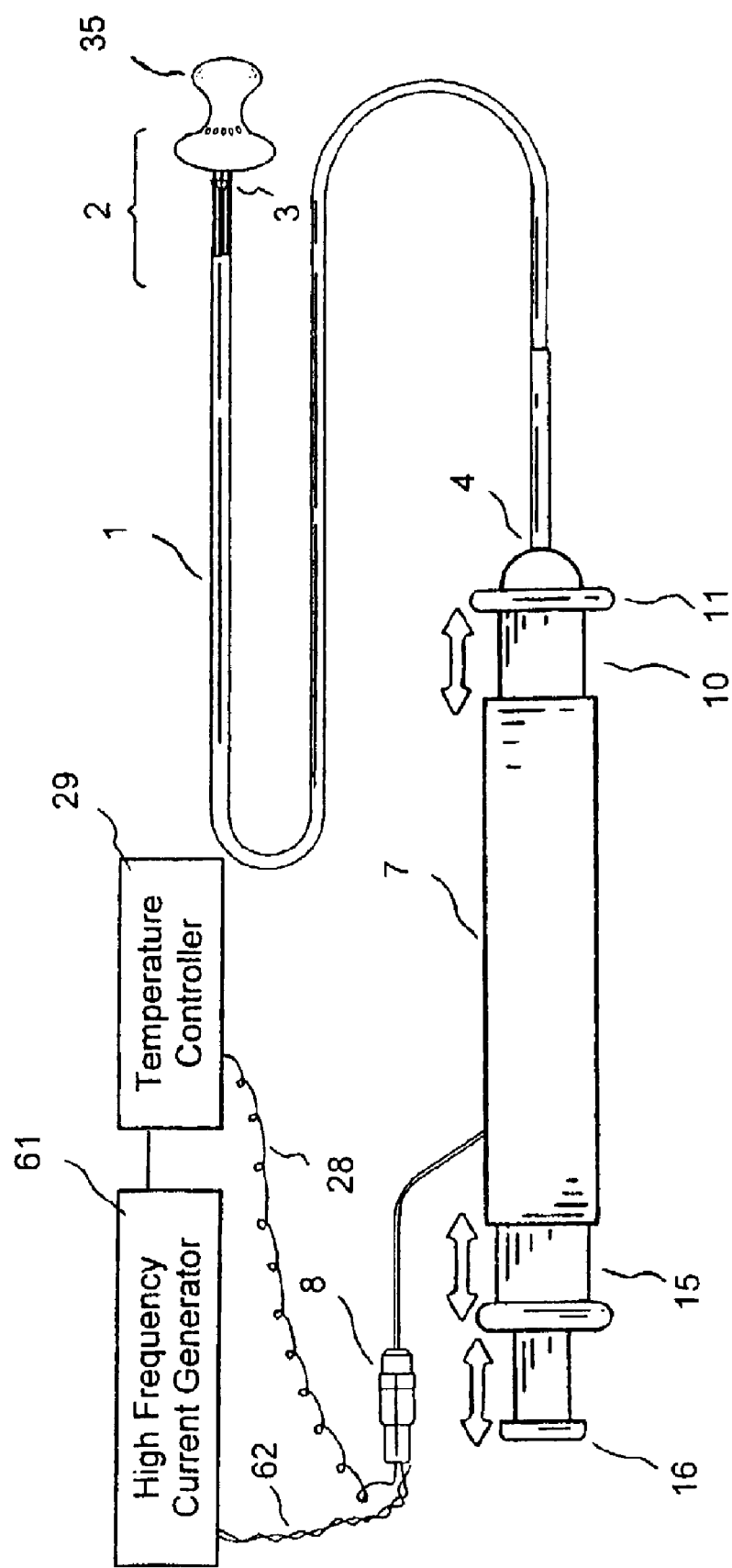
FIG. 1 is a first embodiment of a catheter system having a deployed flexible tissue-contactor member and electrode element means at its distal tip section constructed in accordance with the principles of the present invention.
Figure 2:
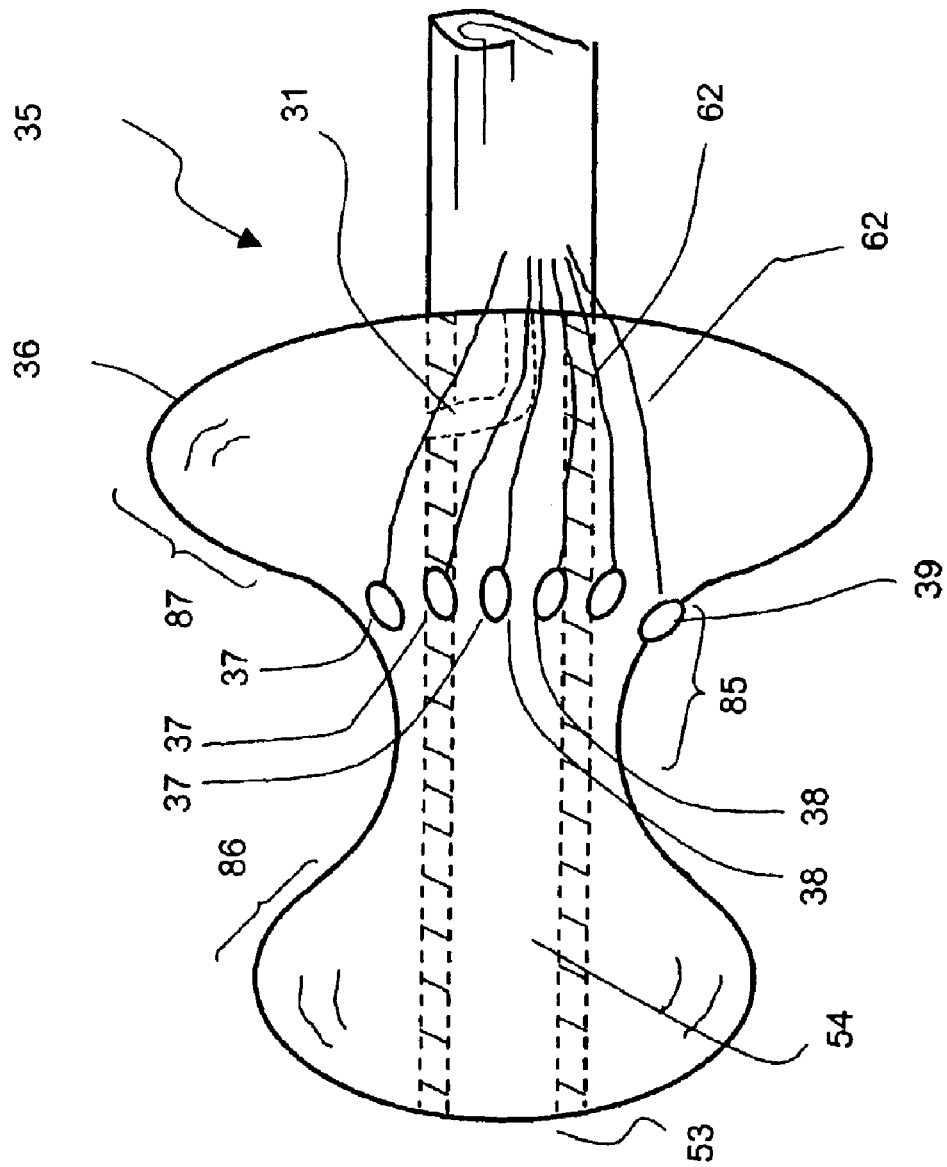
FIG. 2 is a detailed cross-sectional view of the distal tip section of the catheter system according to the first embodiment in FIG. 2, comprising a deployed tissue-contactor member for treating the tissue of an annular organ structure.

FIG. 1 shows a first embodiment of a catheter system having a flexible tissue-contactor member 35 and electrode element means at its distal tip section 2 constructed in accordance with the principles of the present invention. As disclosed in the current invention, the tissue-contactor member 35 is generally configured to be retracted within one of the at least one lumen 14 during catheter insertion into and removal from the patient FIG. 2 shows a detailed cross-sectional view of the distal tip section 2 of the catheter system according to FIG. 1, comprising a deployed tissue-contactor member 35 for treating the tissue of an annular organ structure. In a first embodiment, the tissue-contactor member 35 may comprise a "double-mound" shaped balloon made of flexible expandable biocompatible material selected from a group consisting of silicone, latex, polyurethane, fluoro-elastomer, polypropylene, polyethylene, polyethylene terephthalate, nylon, and a combination thereof. The "double-mound" shape structure of the tissue-contactor member 35 or 45 is related generally to a structure that the tissue-contactor member is deployable out of the lumen of a catheter shaft and is expandable upon deployment configured to have a narrow middle region between an enlarged distal region and an enlarged proximal region (the so called "double-mound" structure) suitable for compressively sandwiching the inner wall of the annular organ structure.

The basic principle for the tissue-contactor member (such as 5 in FIG. 9, 35 in FIG. 1, 45 in FIG. 3, or 95 in FIG. 7) of the present invention is to compress the target tissue (annulus, sphincter, tumor and the like) for enhanced heat shrinkage/tightening on tissue. The compression may come from sandwich type setup, such as from two opposite elements with the target tissue in between or from two elements at a suitable angle arrangement to compress the target tissue. In another embodiment, the "compressively sandwiching" a tissue is also herein intended to mean compression from two elements at a suitable angle arrangement to compress the target tissue as shown by two pairs of electrode elements (FIG. 8): the first electrode elements 96 compressing forwardly toward the distal end 53 and the second electrode elements 98 compressing radially toward the side of the target tissue.

In one illustrative example, the tissue-contactor member 35 in FIG. 2 as an expanded balloon comprises a radially enlarged proximal region 87, a middle region 85, and a radially enlarged distal region 86. The techniques to inflate and deflate a balloon 36 by infusing physiological liquid through a liquid passageway within the lumen 54 and the infusion opening 31 are well known to one who is skilled in the art and do not form a part of the present invention. The tissue-contactor member 35 may comprise a plurality of flexible electrode elements, wherein the electrode elements may be grouped 37, 38 or 39 for performing various modes of energy delivery selected from the group consisting of individual mode, pulsed mode, programmed mode, simultaneous mode, or combination thereof. The flexible electrode elements 37, 38, 39 may be made of conductive elastomer material or metal-containing conductive elastomer material selected from the group consisting of silicone, latex, polyurethane, fluoro-elastomer, nylon, and a combination thereof. The flexible electrode elements normally have similar expansion coefficient as that of the base balloon material and are securely bonded to the surface of the balloon 36 at appropriate locations so that each electrode becomes an integral part of the general tissue contractor member 35. In the first embodiment, the balloon 36 may have an essentially hyperbolic shape with a neck region adapted for positioning the neck region at about the inner wall of the annular organ structure, wherein the plurality of electrode elements (37, 38 or 39 in FIG. 2) are positioned at about the neck region.

Figure 3:
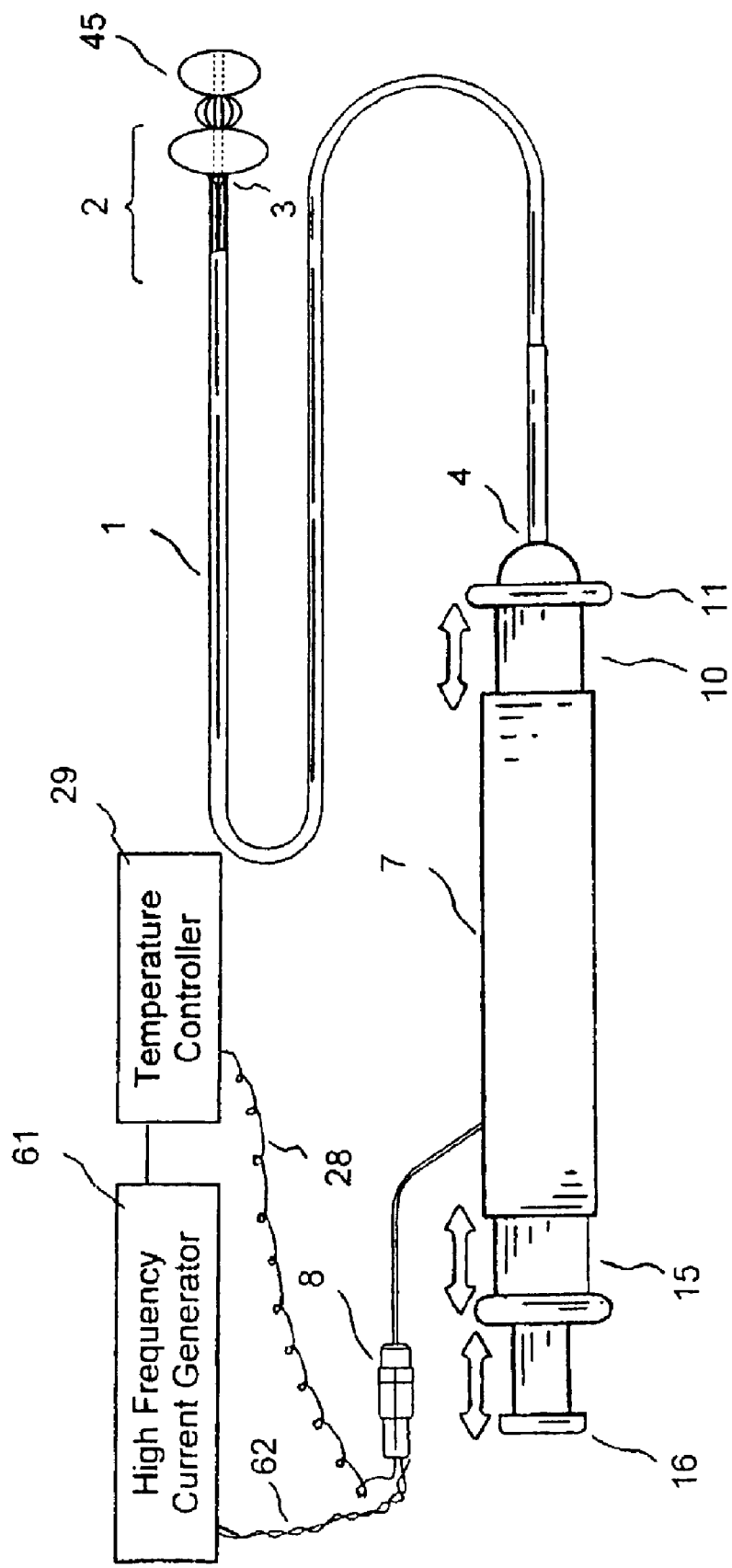
FIG. 3 is a second embodiment of a catheter system having a deployed flexible tissue-contactor member and electrode element means at its distal tip section constructed in accordance with the principles of the present invention.
Figure 4:
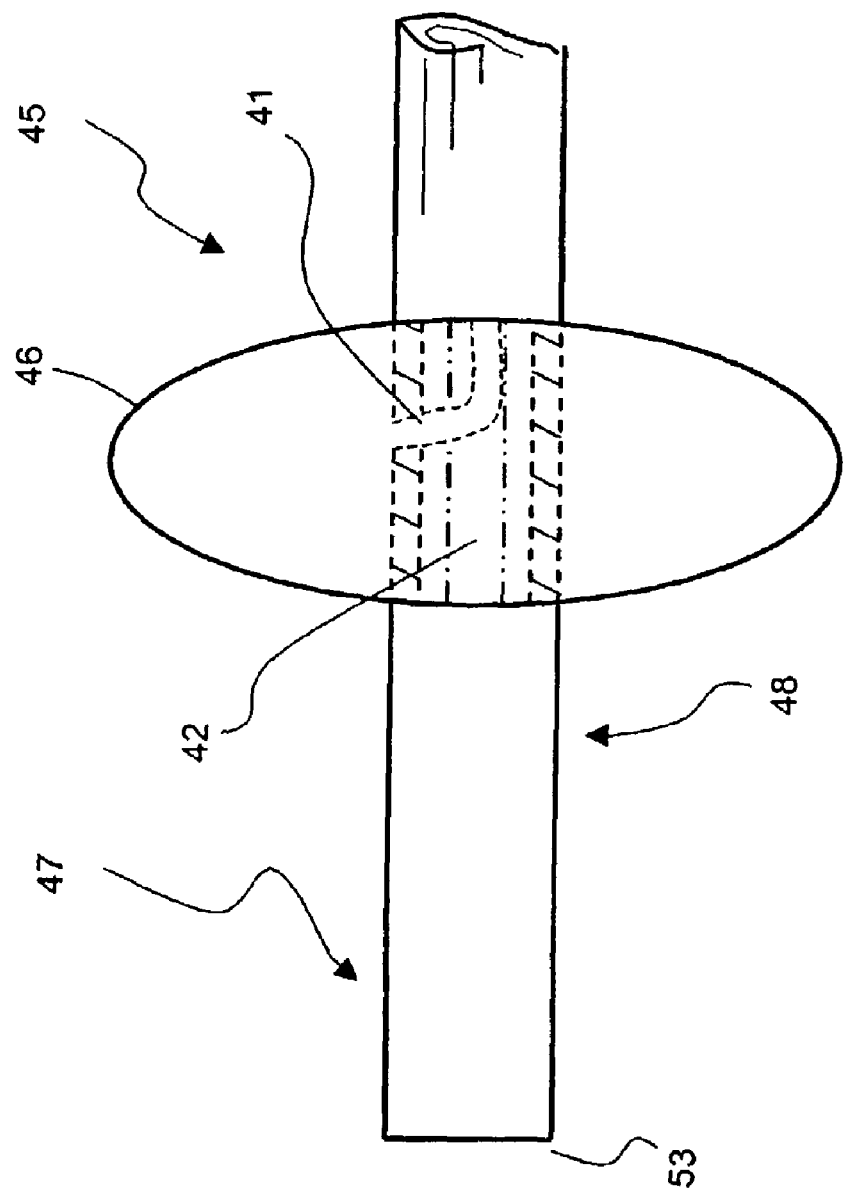
FIG. 4 is a first step of deploying a tissue-contactor member of the catheter system according to the second embodiment in FIG. 3 for treating the tissue of an annular organ structure.
Figure 5:
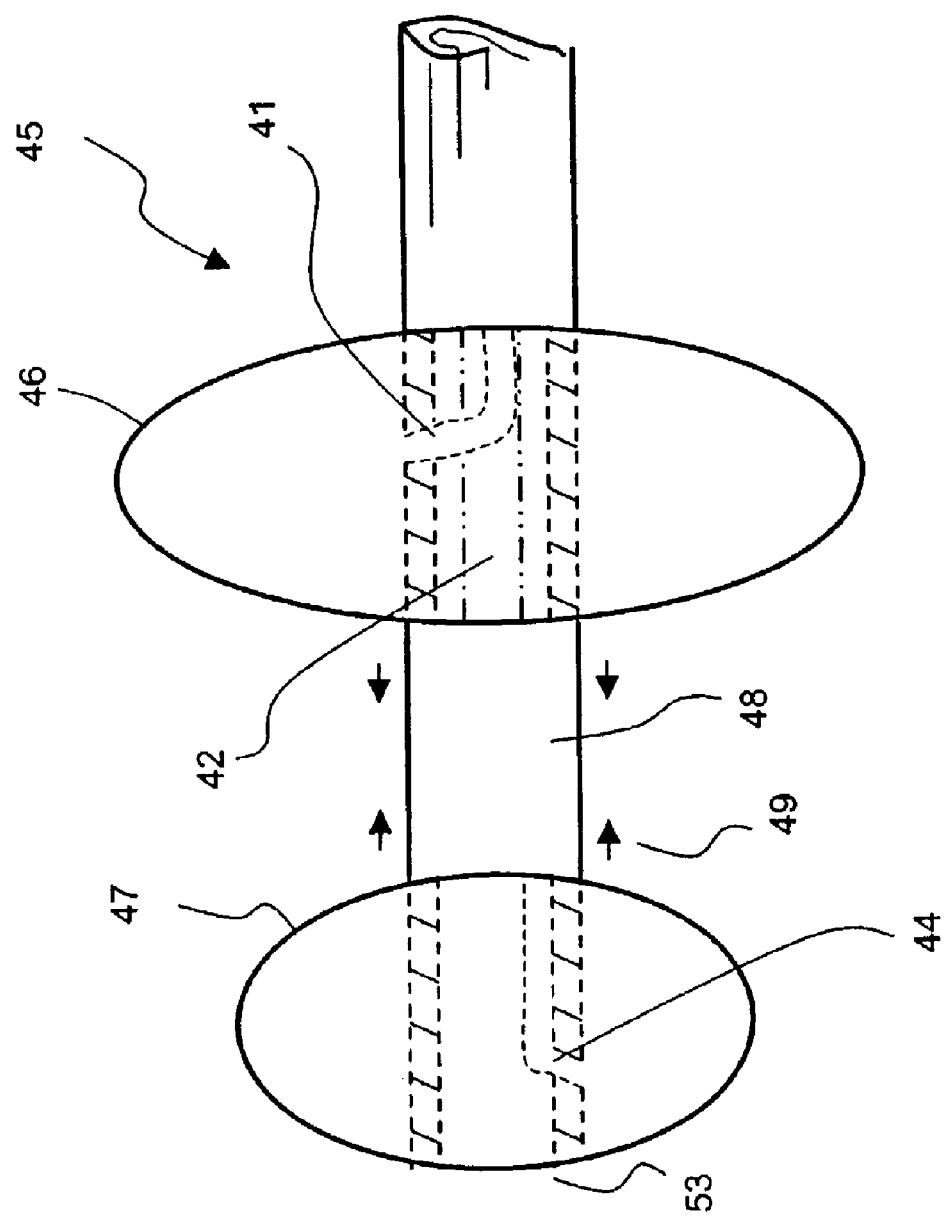
FIG. 5 is a second step of deploying a tissue-contactor member of the catheter system according to the second embodiment in FIG. 3 for treating the tissue of an annular organ structure.
Figure 6:
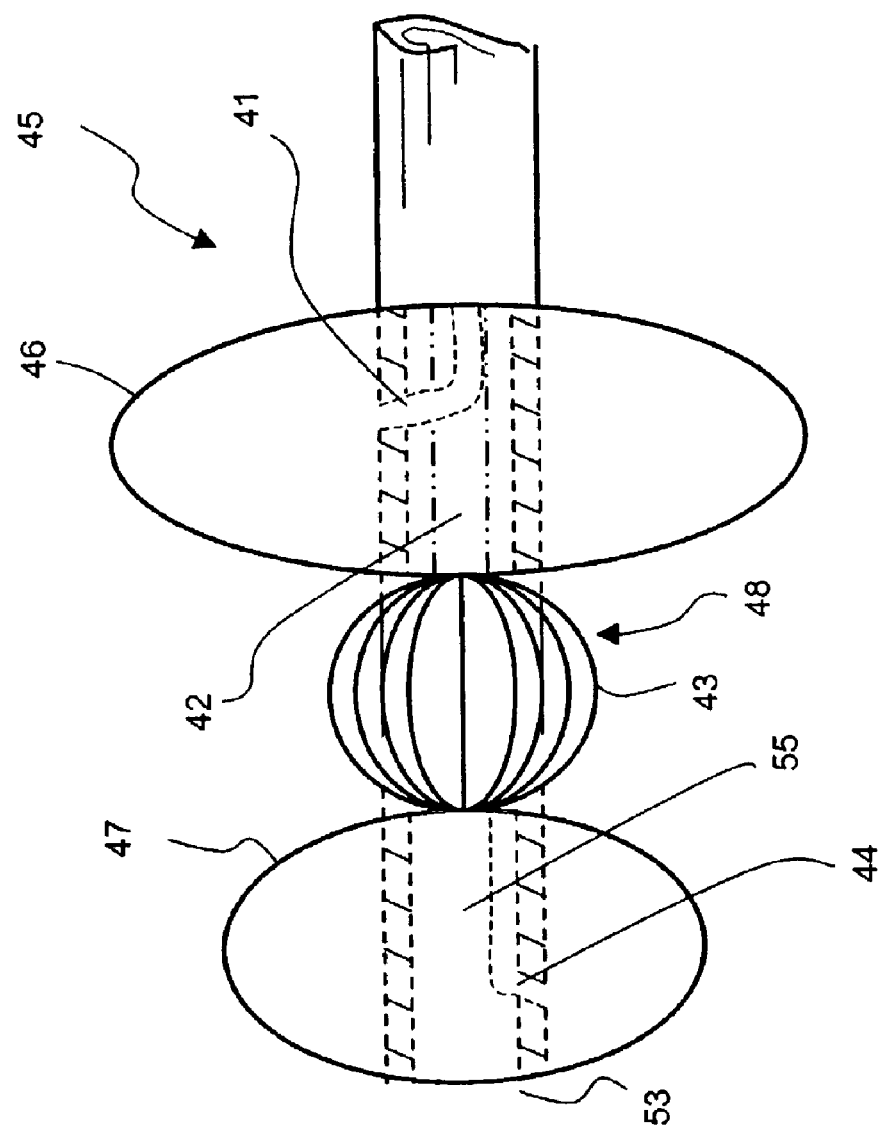
FIG. 6 is a third step of deploying a tissue-contactor member of the catheter system according to the second embodiment in FIG. 3 for treating the tissue of an annular organ structure.

FIG. 3 shows a second embodiment of a catheter system comprising a flexible tissue-contactor member 45 having electrode element means at its distal tip section 2 constructed in accordance with the principles of the present invention. The steps for deploying the tissue-contactor member 45 are illustrated in FIGS. 4 to 6. FIG. 4 shows a first step of deploying a tissue-contactor member 45 of the catheter system 1 according to the second embodiment in FIG. 3 for treating the tissue of an annular organ structure. The flexible tissue-contactor member 45 comprises a proximal balloon 46 as the enlarged proximal region, the distal balloon 47 as the enlarged distal region, and a basket electrode element means 48 as the middle region. The outer diameter of the basket electrode element means 48 of the middle region is smaller than that of either enlarged end region 46, 47 so that the annulus is "compressively sandwiched" for tissue treatment.

The techniques to inflate and deflate a balloon 46 or 47 by infusing physiologic liquid through the liquid passageway 41 or 44 inside a lumen 55 are well known to one who is skilled in the art and do not form a part of the present invention. The physiologic liquid may also comprise contrast medium for enhanced imaging. Other types of balloons, such as a double-balloon, porous balloon, microporous balloon, channel balloon, balloon with heterogeneous construct, or the like that meet the principles of the present invention may be equally herein applicable.

After the first balloon 46 is inflated and sits appropriately at the upstream side of the annulus, a second balloon 47 is also inflated subsequently. At this moment of operations, the annulus of the annular organ structure is positioned loosely between the two end balloons 46 and 47. By relaxing or compressing axially the middle section therebetween (indicated by the arrows 49 in FIG. 5), the annulus is "compressively sandwiched" as defined in the present invention. A "sandwiched" annulus of the present invention generally exhibits certain degree of tightness or compressing.

FIG. 6 shows a third step of deploying a tissue-contactor member 45 of the catheter system according to the second embodiment in FIG. 3 for treating the tissue of an annular organ structure, comprising deployment of the electrode element means 48. The electrode element means 48 may comprise a plurality of basket members that are expandable radially outwardly with a conductive surface 43 on each basket member facing outwardly. Other surface areas of the basket members away from the conductive surface 43 are insulated and not conductive. As disclosed and well known to a skilled artisan, an electrical conductor means 62 for transmitting high frequency current from a high frequency current generator 61 to the electrode elements 48 is provided.

In a embodiment, a method for operating a catheter system of the present invention for repairing a valvular annulus, the method may comprise: (a) percutaneously introducing the catheter system through a blood vessel to a site of the valvular annulus or introducing the catheter system through a thoroscopy port into a heart or optionally injecting the heat shapeable biomaterial during an open-heart surgery; (b) positioning the tissue-contactor member of the catheter shaft on the inner wall of the valvular annulus; (c) advancing the electrode elements for contacting the electrode elements with tissue of the valvular annulus; (d) optionally injecting heat shapeable biomaterial at the site of the valvular annulus defect; and (e) applying high frequency current through the electrical conductor means to the electrode elements for repairing the valvular annulus defect.

Figure 7:
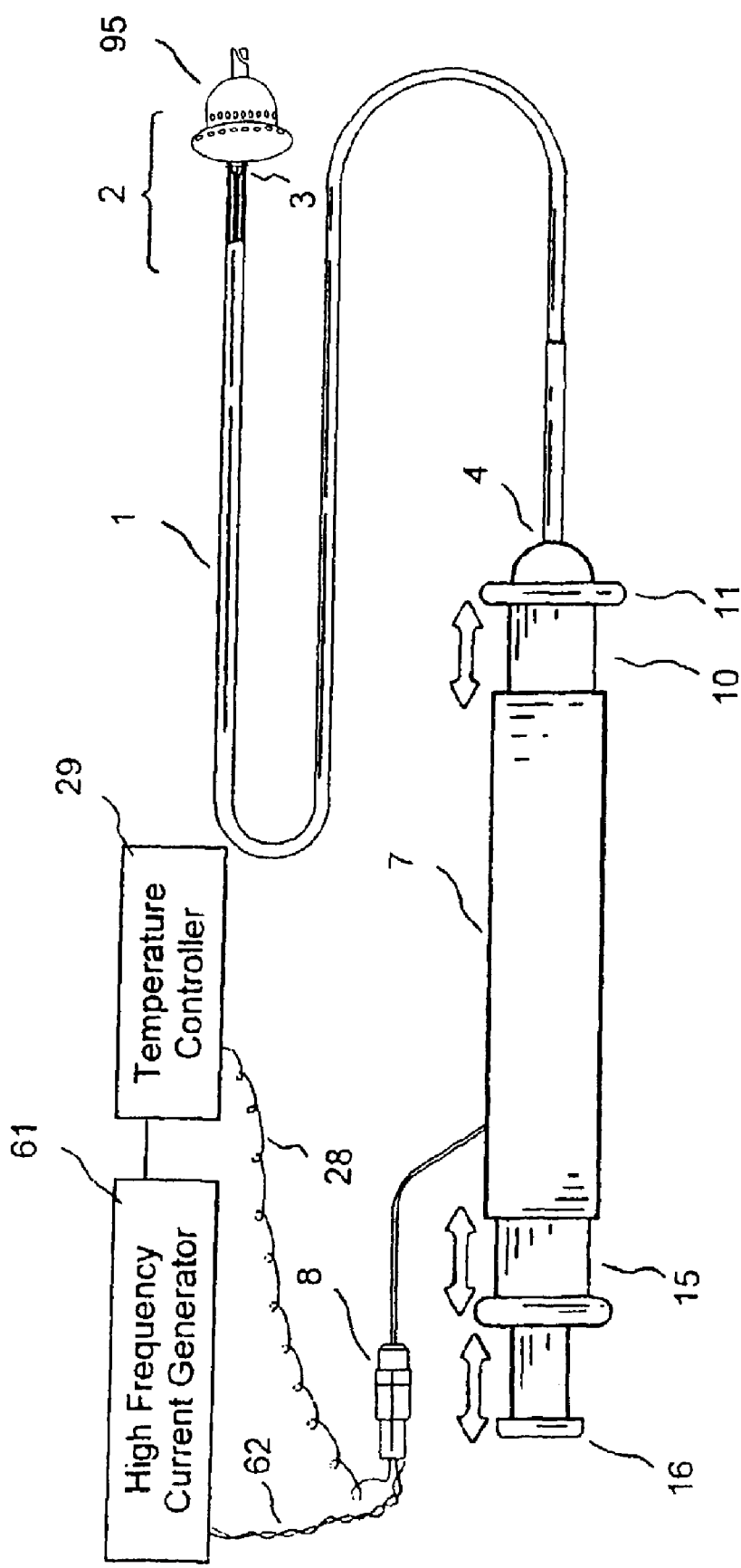
FIG. 7 is a third embodiment of a catheter system having a deployed flexible tissue-contactor member and electrode element means at its distal tip section constructed in accordance with the principles of the present invention.

FIG. 7 shows a third embodiment of a catheter system having a deployed flexible tissue-contactor member 95 and electrode element means at its distal tip section constructed in accordance with the principles of the present invention. The acorn-shaped tissue-contactor member 95 is to compressively sandwich a target annulus from two sides of the annulus at about 90 degrees to each other.

Figure 8:
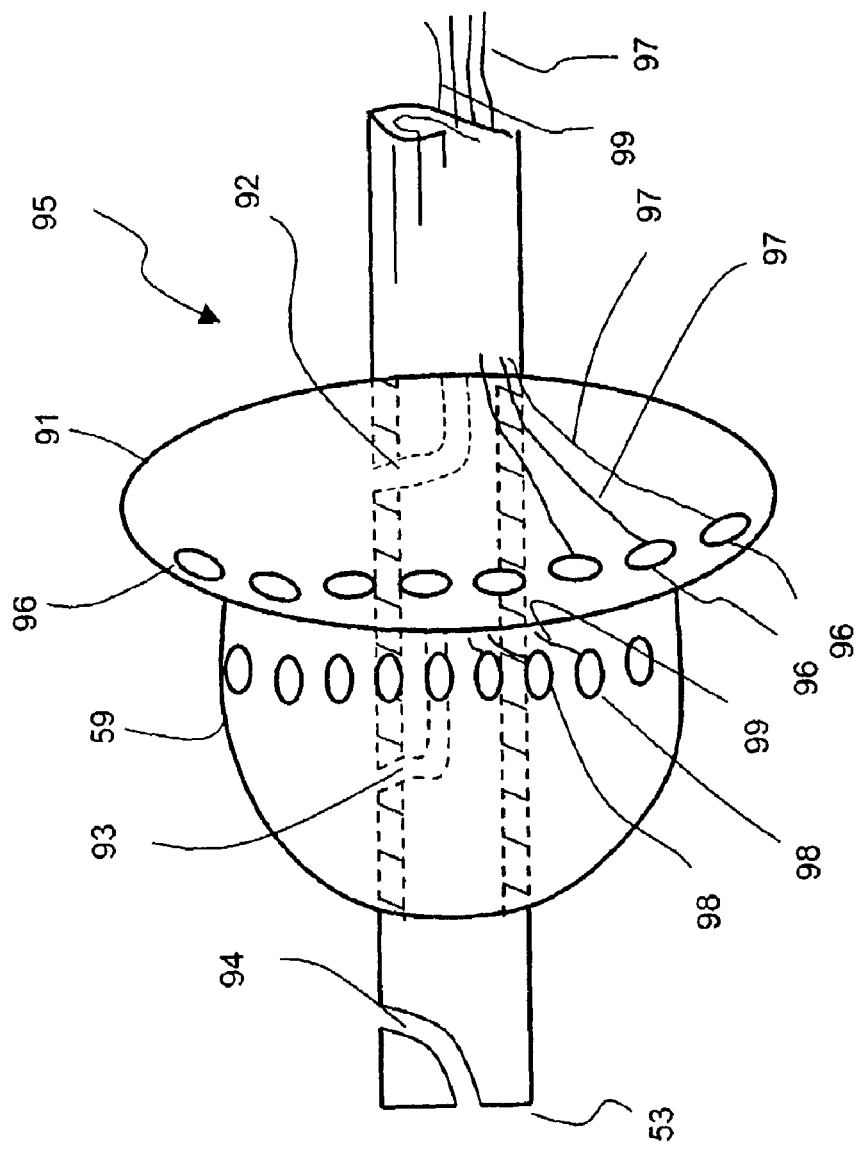
FIG. 8 is a detailed cross-sectional view of the distal tip section of the catheter system according to the third embodiment in FIG. 7, comprising a deployed tissue-contactor member for treating the tissue of an annular organ structure.

FIG. 8 shows a detailed cross-sectional view of the distal tip section 2 of the catheter system 1 according to the third embodiment in FIG. 7, comprising a deployed tissue-contactor member 95 for treating the tissue of an annular organ structure. In an example of mitral annulus treatment for illustration purposes, the first balloon 91 is intended to lie on top of the annulus while the flexible electrode elements 96 made of conductive elastomer material are intended to provide sufficient therapeutic energy for treating the annulus. The second balloon 59 is intended to lie against the inner wall of the annulus so that the flexible electrode elements 98 made of conductive elastomer material are intended to provide sufficient therapeutic energy for treating the leaflets. As is well known to one who is skilled in the art of balloon construction and the high frequency ablation technology, an electrical conductor means 97 or 99 for transmitting high frequency current to each electrode 96 or 98 is provided individually to the energy source while physiologic liquid to each balloon 91, 59 through a liquid passageway 92, 93 is also provided.

In an alternate embodiment, the flexible electrode elements 96, 98 may comprise a plurality of discrete elements, a plurality of contiguous elements, or a plurality of discrete element groups, each group comprising at least one electrode element. The arrangement of different styles of electrode elements is to facilitate treating a desired portion or a complete annular tissue under various modes. It is also well known to one skilled in the art that the flexible electrode means of the present invention may be constructed of an elongate flexible conductive electrode or with a conductive surface. In one example, an elongate flexible conductive electrode may comprise a metal-containing elastic (stretchable) electrode made of similar constructing material of the balloon. In a further embodiment, the elongate flexible conductive electrode may be a separate conductive elastic band (like a party rubber band) that is deployed between the exterior surface of the balloon and the inner wall of the annulus. The elongate flexible conductive electrode may be one type of the strip electrodes.

One advantage of the current embodiment in FIG. 8 is to provide physiologic liquid to inflate a balloon for repairing the valvular defect, whereas the liquid in the balloon serves as a heat sink to dissipate the heat generated from the high frequency electrode elements contacting the tissue. In one aspect, the physiologic liquid of the present invention is a high thermally conductive fluid for heat transmission. By continuously diverting the excess heat from the electrode tissue contact site, the treatment efficiency can be substantially enhanced to cause quality desired shrinkage or tightening of the tissue of the annulus. The requirement for the high frequency power can therefore be significantly reduced. The energy required from the high frequency current generator is generally less than 100 watts in tissue ablation, preferably less than 10 watts because of the heat dissipating embodiment of the present invention for repairing an annulus.

The catheter system of the present invention may also comprise a guidewire adaptive mechanism, such as a guidewire channel 94 located at about the balloon distal end 53 in FIG. 8 for the catheter to ride on a guidewire to the desired location for tissue treatment.

Figure 9:
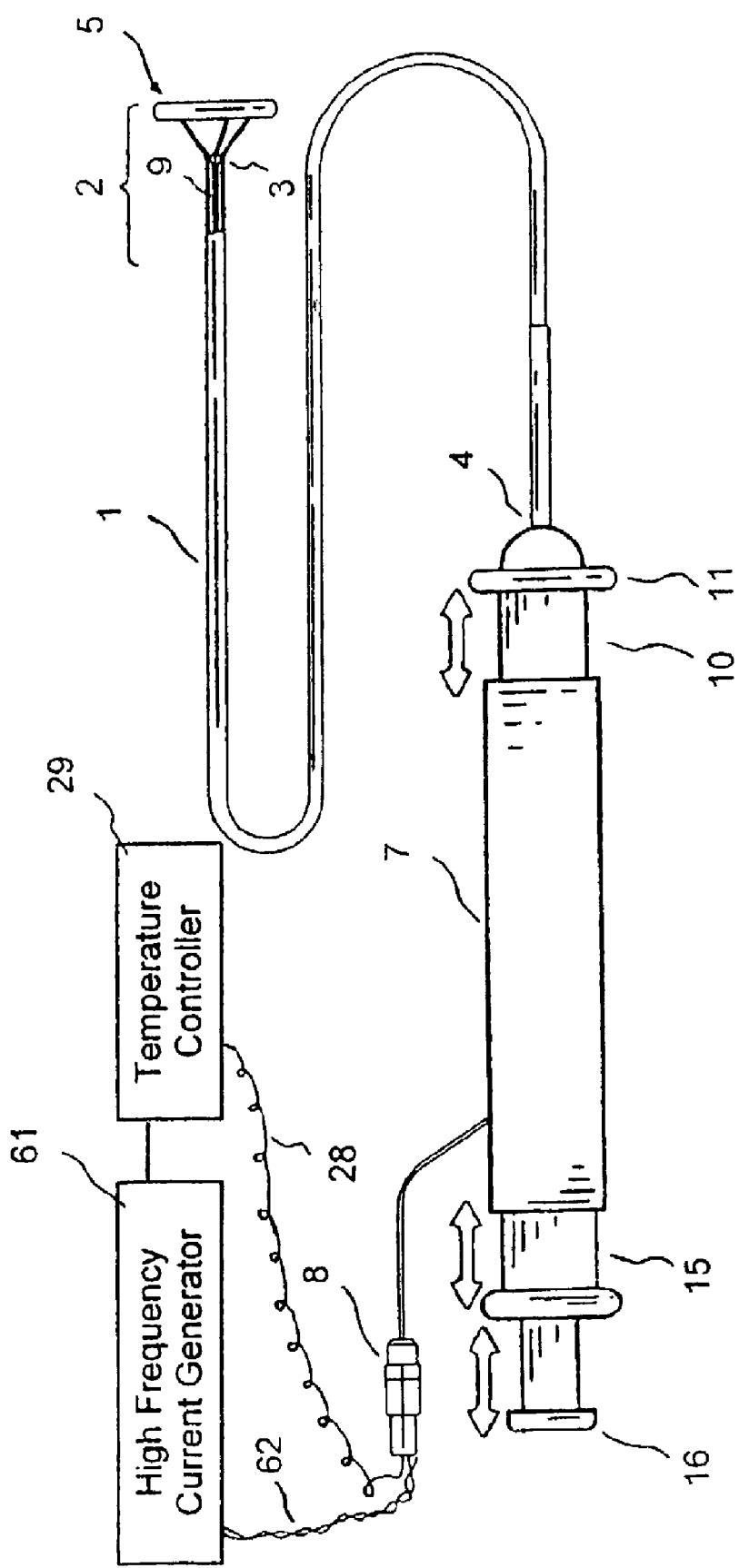
FIG. 9 is an overall view of a catheter system having a flexible tissue-contactor member and electrode element means at its distal tip section constructed in accordance with the principles of the present invention.

FIG. 9 shows an overall view of one embodiment of a catheter-based high-frequency treatment system having a flexible tissue-contactor member and an electrode element means at its distal tip section constructed in accordance with the principles of the present invention. A catheter system constructed in accordance with the principles of the present invention comprises a flexible catheter shaft 1 having a distal tip section 2, a distal end 3, a proximal end 4, and at least one lumen 14 extending therebetween.

In one aspect, the catheter system comprises a tissue-contactor member 5 that is flexible, relatively semi-rigid located at the distal tip section 2 and inside the at least one lumen 14 of the catheter shaft 1 for contacting an inner wall 51 of an annular organ structure 52 when deployed. The tissue-contactor members may have certain variations (35 in FIG. 1, 45 in FIG. 3, 110 in FIG. 16, and 130 in FIG. 19) sharing the common characteristics of contacting the annulus intimately while delivering tissue-shrinkable energy. In some aspects, the tissue contactor member may particularly have a narrow middle region between a first radially enlarged proximal region and a second radially enlarged distal region suitable for compressively sandwiching the inner wall 51 of the annular organ structure 52 for effectively applying tissue-shrinkable energy site specifically. It is believed that "compressively sandwiching the inner wall of the annular organ structure" is one of significant requirements for effectively applying tissue-shrinkable energy site specifically.

The tissue-contactor member 5 is deployable out of the at least one lumen 14 by a tissue-contactor deployment mechanism 15 located at a handle 7. The tissue-contactor member 5 is preformed or expandable to have an appropriate shape configured to fit with the inner wall 51 of the annular organ structure 52. The tissue-contactor member 5 may be selected from the group consisting of a circular ring, a semi-circular, a D-shaped ring, a kidney-shaped ring, an oval ring, a C-shaped ring, a double-loop balloon ring, and other round-shaped construct configured for effectively contacting the annulus to be treated.

The handle 7 is attached to the proximal end 4 of the catheter shaft 1. The handle comprises the tissue-contactor deployment mechanism 15 and an electrode deployment means 16 for advancing the electrode element means 9 out of the tissue-contactor member 5. The electrode element means intended for shrinking tissue of an annular organ structure may comprise needle electrodes 9 in FIG. 14, or other variations such as the one made of conductive elastomer material on a balloon (37, 38, 39 in FIG. 2), a basket electrode element 48 in FIG. 6, the "acorn" electrode elements 96, 98 in FIG. 8, the strip electrodes 114 in FIG. 17, and the strip electrodes 137 in FIG. 19. A strip electrode is generally an electrode having its energy-releasing surface contacted target tissue.

A connector 8 secured at the proximal end of the catheter system, is part of the handle section 7. The handle has one optional steering mechanism 10. The steering mechanism 10 is to deflect the distal tip section 2 of the catheter shaft 1 for catheter maneuvering and positioning. In one embodiment, by pushing forward the front plunger 11 of the handle 7, the distal tip section 2 of the catheter shaft deflects to one direction. By pulling back the front plunger 11, the tip section returns to its neutral position. In another embodiment, the steering mechanism 10 at the handle 7 comprises means for providing a plurality of deflectable curves on the distal tip section 2 of the catheter shaft 1.

The catheter system also comprises a high frequency current generator 61, wherein an electrical conductor means 62 for transmitting high frequency current to the electrode element means (9 in FIG. 9, 35 in FIG. 1 or 45 in FIG. 3) is provided. One object of the present invention is to provide high frequency heat to collagen of tissue to a temperature range of about 45° C. to 75° C. or higher for at least a few seconds to cause collagen to shrink a fraction of its original dimension. The energy required from the high frequency current generator is generally less than 100 watts, preferably less than about 10 watts.

The high frequency current may be selected from a group consisting of radiofrequency current, microwave current, focused ultrasound current, and combination thereof. Tu in U.S. Pat. No. 6,235,024, entire contents of which are incorporated herein by reference, discloses a catheter system having dual ablation capability of ultrasound current and radiofrequency current. The electrode element of the present invention may comprise a radiofrequency electrode, a focused ultrasound electrode (that is, transducer) or a combination thereof.

Laufer in U.S. Pat. No. 6,083,219, entire contents of which are incorporated herein by reference, discloses a device for treating damaged heart valve leaflets using simple ultrasound energy applied to the desired tissue. However, Laufer '219 does not disclose a focus ultrasonic energy that applied remotely to the target tissue with little effects on the surrounding tissue. Naghavi et al. in U.S. Pat. No. 6,451,044, entire contents of which are incorporated herein by reference, discloses applying focused ultrasound energy for treating inflammation. However, Naghavi et al. '044 does not disclose a method of treating valvular annulus using focused ultrasound energy from a tissue contact member or means.

Conventional ultrasound thermal therapy has been used for heat delivery to a non-targeted tissue, to achieve coagulation and clot formation in surgery, and for physical therapy. High intensity focused ultrasound is effective for heating a target tissue within a predetermined distance of scope, typically increasing the temperature of the target tissue by about 10-20° C. or higher. High intensity ultrasound is also used to stop bleeding, in lithotripsy procedures, and for deep surgery. Generally, in tissues where heat removal by blood flow or by conduction is significant, higher energy pulsed beams of focused ultrasound are sometimes employed in order to remotely achieve the desired level of heating at a target site away from the flowing blood. Conventional ultrasound thermal energy may be applied to treat annulus, but is less desirable because of heat dissipation by the flowing blood.

Tu in U.S. Pat. No. 6,267,781 teaches an ablation device for treating valvular annulus or valvular organ structure of a patient, comprising a flexible elongate tubular shaft having a deployable spiral wire electrode at its distal end adapted to contact/penetrate the tissue to be treated and to apply high frequency energy to the tissue for therapeutic purposes. Further, Tu et al. in U.S. Pat. No. 6,283,962 discloses a medical ablation for treating valvular annulus wherein an elongate tubular element comprises an electrode disposed at its distal section that is extendible from an opening at one side of the tubular element, the energy generator, and means for generating rotational sweeping force at the distal section of the tubular element to effect the heat treatment and the rotational sweeping massage therapy for target tissues. Tu et al. in U.S. Pat. No. 6,306,133 discloses an ablation catheter system and methods for repairing an annular organ structure comprising high frequency ablation for the purposes of tightening and stabilizing a tissue.

A catheter suitable for high frequency ablation comprises a flexible tissue-contactor means located at the distal tip section of a catheter shaft for contacting an inner wall of the annular organ structure, and a needle electrode means located at or within the flexible tissue contactor means for penetrating into the tissue, wherein the needle electrode means is deployable out of the tissue-contactor means in a manner essentially perpendicular to a longitudinal axis of the catheter shaft. All above three patents (U.S. Pat. Nos. 6,267,781, 6,283,962, and 6,306,133), entire contents of which are incorporated herein by reference, teach only the local tissue shrinkage, not for treating a substantial portion of the valvular annulus via a deep penetrating focused ultrasound energy.

Therefore, a method is disclosed herein to treat an annual organ structure of a heart valve, a venous valve, a valve leaflet, a valvular annulus, chordae tendinae, papillary muscles, esophageal sphincter, and the like by a dual RF & ultrasound ablation system. The RF energy is applied directly to the tissue while ultrasound energy and microvibration therapy are applied deep into the adjacent tissue of tissue at a short distance. U.S. Pat. No. 6,235,024, entire contents of which are incorporated herein by reference, to one of co-inventors discloses an improved ablation catheter system comprising an ablation element on a distal section of an elongate catheter tubing, the ablation element having dual capability of radiofrequency ablation and ultrasound ablation, the ablation element comprising an ultrasound transducer, a conductive outer surface and a conductive inner surface, the ablation catheter system further comprising a high frequency energy generator means which has a switching means for switching the ablation operation mode to a radiofrequency ablation mode, an ultrasound ablation mode, or a simultaneous radiofrequency and ultrasound ablation mode.

Hissong in U.S. Pat. No. 6,361,531 discloses a focused ultrasound ablation device. Tu et al. in U.S. Pat. No. 6,206,842 discloses an ultrasound ablation device. Tu et al. in U.S. Pat. No. 6,235,024 discloses a dual ablation catheter system. All above three patents, entire contents of which are incorporated herein by reference, disclose focused ultrasound ablation energy for remotely heating a tissue.

Prior focused ultrasound ablation devices have been designed to access anatomical sites at which ultrasound emitting members of the devices must be placed in order to ablate designated target areas. For example, some prior focused ultrasound ablation devices, of which U.S. Pat. No. Re. 33,590, U.S. Pat. Nos. 4,658,828, 5,080,101, 5,080,102, 5,150,712 and 5,431,621 are representative, are designed as structure for being positioned over and/or attached to a patient's skull. As another example, some prior focused ultrasound ablation devices have been designed as part of a table or support on which a patient is disposed or as structure positioned over such a table or support as represented by U.S. Pat. Nos. 4,951,653, 5,054,470 and 5,873,845. As a further example, U.S. Pat. Nos. 5,295,484, 5,391,197, 5,492,126, 5,676,692, 5,762,066 and 5,895,356 are illustrative of focused ultrasound ablation devices having ultrasound emitting members carried in, on or coupled to flexible shafts, probes or catheters insertable in anatomical lumens, with the shafts, probes or catheters naturally conforming to the configurations of the anatomical lumens. U.S. Pat. Nos. 5,150,711, 5,143,074, 5,354,258 and 5,501,655 are representative of focused ultrasound ablation devices having portions thereof placed against or in contact with patients' bodies.

In one embodiment of less invasive tissue treatment, a tissue treatment method for treating cellular tissue of an annular organ structure comprises the steps of: (a) inserting a medical catheter device into a coronary vein through coronary sinus of a patient, wherein the medical catheter device comprises at least one ultrasonic transducer mounted on the distal section thereof, (b) positioning the medical catheter device to place one of the at least one ultrasonic transducer at a distance to a tissue region (such as a mitral annulus) to be treated, wherein the at least one ultrasonic transducer is adapted to be placed in a short distance from cellular tissues; (c) activating the ultrasonic transducer to direct ultrasonic energy toward the tissue region to be treated, thereby generating effective thermal energy and microvibration (inherently from ultrasound generation) in the cellular tissues; and (d) heating the cellular tissues by the focused ultrasound energy to a temperature and depth sufficient to tighten and shrink the cellular tissues, thereby therapeutically treating the cellular tissues. In one embodiment, the ultrasound transducer is capable of emitting ultrasound energy and focusing the ultrasound energy at one or more focusing zones within a target area in the tissue. In another embodiment, the transducer is located at a predetermined distance in front of the active face configured for heating the tissue at the target area with the focused ultrasound energy to tighten and stabilize an annular organ structure adapted for repairing an annular organ structure defect of a patient. This focused energy targeting may be assisted with an Ultrasound Locating System discussed below.

In other embodiment of non-invasive tissue treatment, a tissue treatment method for treating cellular tissue of an annular organ structure comprises the steps of: (a) placing a medical system at close proximity while outside of the body of a patient, wherein the medical system comprises at least one ultrasonic transducer mounted at a suitable location on the system thereof (b) positioning the medical system to place the at least one ultrasonic transducer at a distance to a tissue region to be treated inside the body, wherein the at least one ultrasonic transducer is adapted to be placed in a short distance from cellular tissues; (c) activating the ultrasonic transducer to direct ultrasonic energy toward the tissue region to be treated, thereby generating effective thermal energy and microvibration (inherently from ultrasound generation) in the cellular tissues; and (d) heating the cellular tissues to a temperature and depth sufficient to tighten and shrink the cellular tissues, thereby therapeutically treating the cellular tissues. In one embodiment, the ultrasound transducer is capable of emitting ultrasound energy and focusing the ultrasound energy at one or more focusing zones within a target area in the tissue. In another embodiment, the transducer is located at a predetermined distance with the active face facing the target tissue configured for heating the tissue at the target area with the focused ultrasound energy to tighten and stabilize an annular organ structure adapted for repairing an annular organ structure defect of a patient. In still another embodiment, the predetermined distance may comprise a circular ring-shape essentially matching the annular tissue for receiving the focused ultrasound energy for treatment.

In one embodiment, the method may comprise percutaneously introducing the catheter system through a blood vessel to a site of the valvular annulus or introducing the catheter system through a thoroscopy port into a heart or injecting the heat shapeable biomaterial during an open-heart surgery. For other applications such as the sphincter treatment, the catheter may be introduced through a natural opening of the body. The application for sphincter treatment of the present invention comprises esophageal sphincter, urinary sphincter or the like. Small, ring-like muscles, called sphincters, surround portions of the alimentary and urogenital tracts. In a healthy person, for example, some of these sphincter muscles contract or tighten in a coordinated fashion during eating and the ensuing digestive process, to temporarily close off one region of the alimentary canal from another.

For example, a muscular ring called the lower esophageal sphincter surrounds the opening between the esophagus and the stomach. The lower esophageal sphincter is a ring of increased thickness in the circular, smooth-muscle layer of the esophagus. Normally, the lower esophageal sphincter maintains a high pressure zone between fifteen and thirty mm Hg above intragastric pressures inside the stomach. The catheter system and methods of the present invention may suitably apply to repair a sphincter annulus, other than the esophageal sphincter, in a patient.

Figure 10:
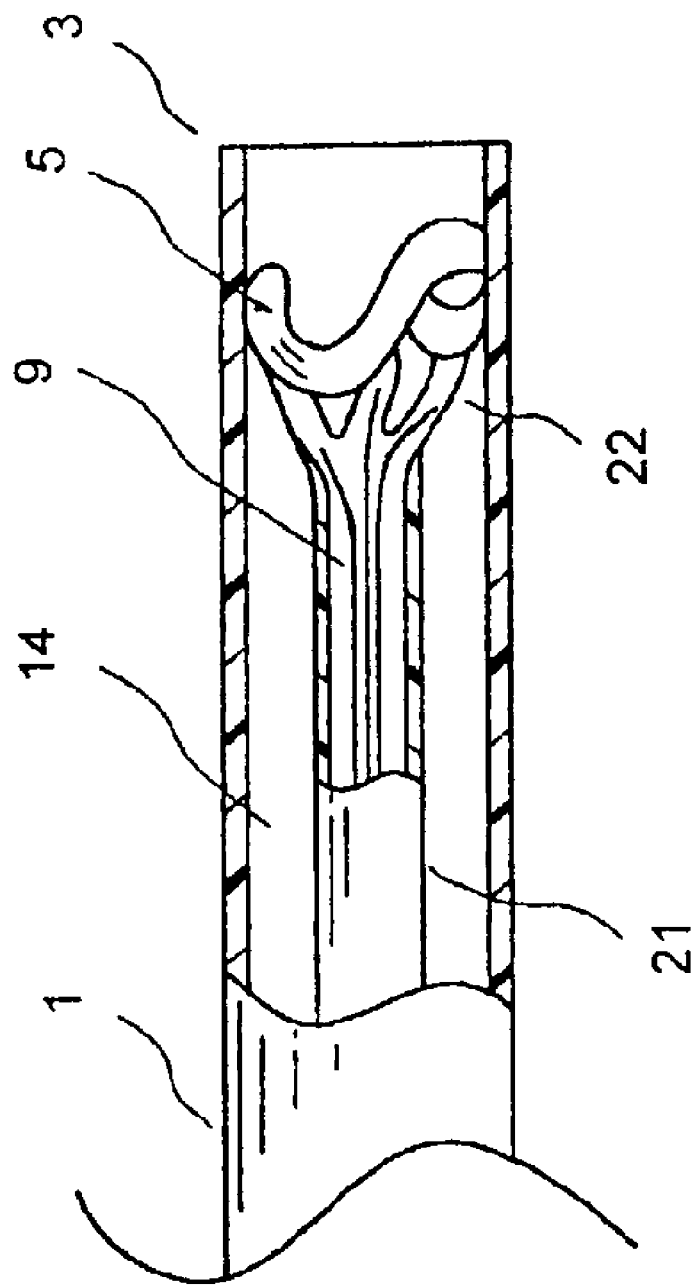
FIG. 10 is a close up view of the distal tip section of the catheter system comprising a retracted tissue-contactor members with a retracted electrode element means at a non-deployed state.

FIG. 10 shows a close up view of the distal tip section 2 of the catheter system comprising a retracted tissue-contactor member 5 with a retracted electrode element means 9 at a non-deployed state. Both the tissue-contactor member and the electrode element means are retractable to stay within the at least one lumen 14. This non-deployed state is used for a catheter to enter into and to withdraw from the body of a patient. The tissue-contactor member is generally preformed or constricted and flexible enough so that it can easily be retracted into the catheter lumen 14.

The tissue-contactor member 5 may be made of a biocompatible material selected from the group consisting of silicone, latex, polyurethane, fluoro-elastomer, polypropylene, polyethylene, polyethylene terephthalate, nylon, and a combination thereof. Reinforced substrate, such as mesh, wire, fiber, and the like, may be added to the tissue-contactor member 5 to make the tissue-contactor member semi-rigid so that when it is deployed, adequate pressure is exerted to the surrounding tissue for stabilizing its placement.

In one particular embodiment, the catheter system may comprise a needle electrode element means 9 located at or within the flexible tissue-contactor member 5 for penetrating into a tissue, such as an inner wall 51, wherein the needle electrode element means 9 is deployable out of the tissue-contactor member 5 in a manner essentially, perpendicular to a longitudinal axis of the catheter shaft 1 when the needle electrode element means is deployed. In another embodiment, the angle of the needle electrode against a tissue may be any suitable angle from 30 degrees to 150 degrees in reference to a longitudinal axis of the catheter shaft for effective tissue penetration.

The needle electrode element means 9 may comprise a plurality of needle electrodes 9A, 9B, 9C (shown in FIG. 14) that are preshaped to be essentially perpendicular to a longitudinal axis of the catheter shaft 1 when deployed. The high frequency current may be delivered to each of the plurality of needle electrodes 9A, 9B, 9C in a current delivery mode selected from the group consisting of individual delivery mode, pulsed delivery mode, sequential delivery mode, simultaneous delivery mode or a pre-programmed mode. The needle electrode element means 9 may be made of a material selected from the group consisting of platinum, iridium, gold, silver, stainless steel, tungsten, nitinol, and other conducting material. The needle electrode element means 9 is connected to an electrode deployment means 16 at the handle 7 for advancing one or more needles of the needle electrode element means 9 out of the tissue-contactor member 5. This electrode deployment means may include various deployment modes selected from a group consisting of a single needle electrode deployment, a plurality of needle electrodes deployment or an all needle electrodes simultaneous deployment.

Figure 12:
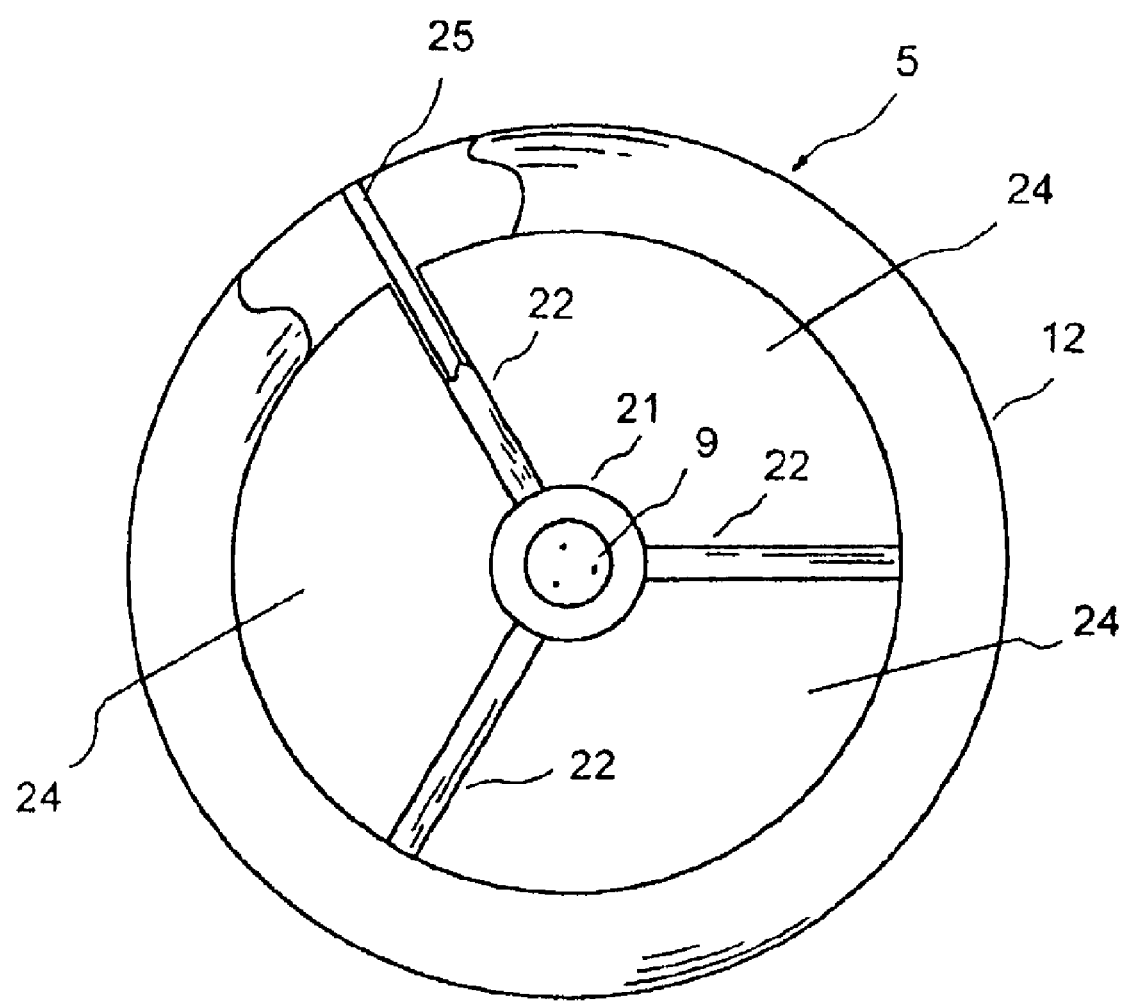
FIG. 12 is a front cross-sectional view, section I-I of FIG. 11, of the distal tip section of a catheter system comprising a deployed tissue-contactor member.

The "tissue-contactor member" in this invention is intended to mean a flexible semi-rigid element adapted for contacting an inner wall of an annular organ structure of a patient and is also preformed to have an appropriate shape compatible with the inner wall of the annular organ structure. The tissue-contactor member 5 may generally comprise a plurality of grooves or internal channels 25 (as shown in FIG. 12) so that a needle electrode of the needle electrode element means is able to deploy out of and retract into the tissue-contactor means with minimal frictional resistance.

Therefore, it is one aspect of the invention to provide a catheter or cannula system for repairing an annular organ structure comprising it flexible catheter shaft or semi-rigid cannula shaft having a distal tip section, a distal end, a proximal end, and at least one lumen extending between the distal end and the proximal end. The system further comprises a flexible tissue-contactor member located at the distal tip section and inside the at least one lumen of the shaft for contacting an inner wall of the annular organ structure, wherein the tissue-contactor member is deployable out of the at least one lumen by a tissue-contactor deployment mechanism and is expandable upon deployment configured to intimately contacting at least a portion of the inner wall of the annular organ structure, the deployed tissue-contactor member moving in a coordinated fashion with movement of the annular organ structure. The catheter or cannula system may further comprise a plurality of energy-delivery elements located at the tissue-contactor, a handle attached to the proximal end of the catheter shaft, wherein the handle comprises the tissue-contactor deployment mechanism, and a high frequency current generator, wherein an electrical conductor means for transmitting high frequency current to the energy-delivery elements is provided.

Figure 11:
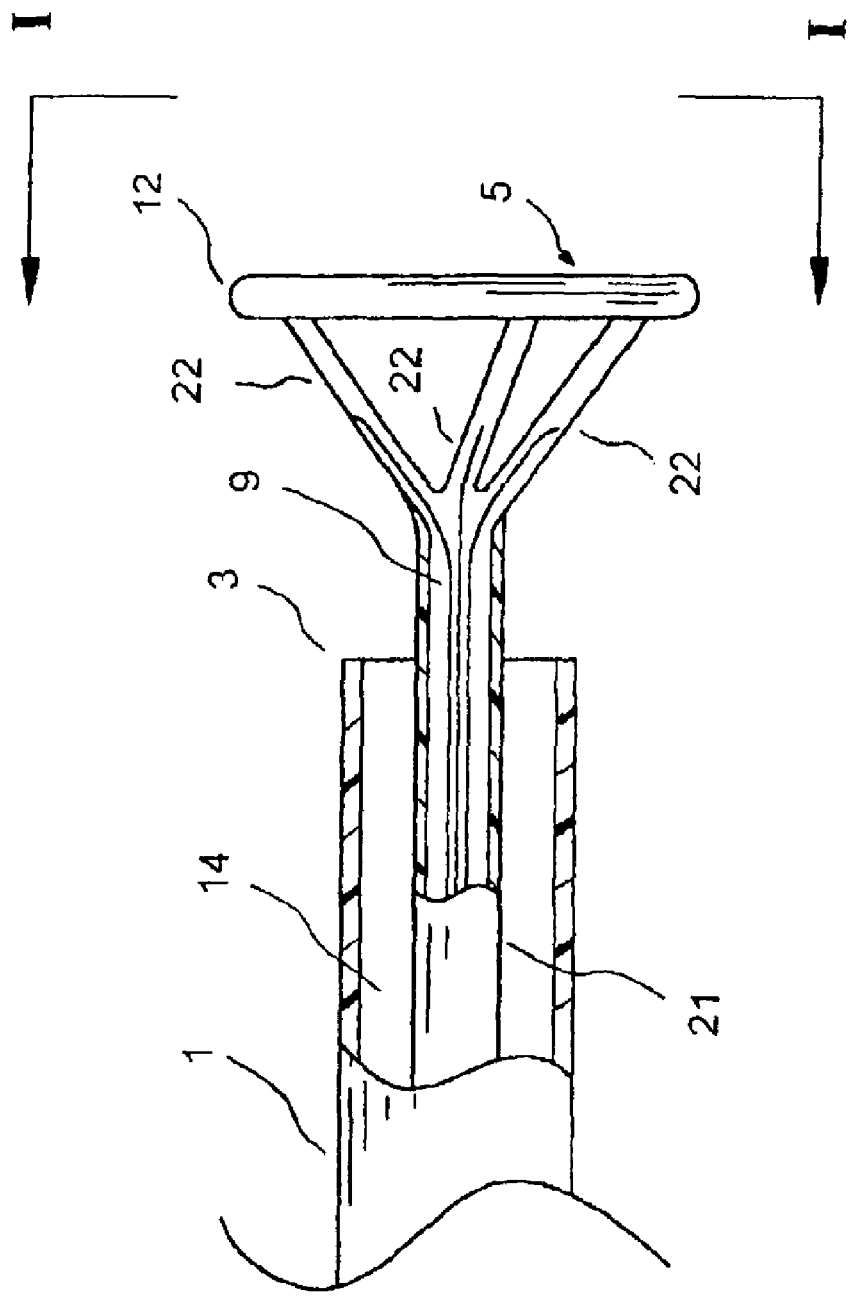
FIG. 11 is a close up view of the distal tip section of the catheter system comprising a deployed tissue-contactor member having a retracted electrode element means.

FIG. 11 shows a close up view of the distal tip section 2 of one embodiment of the catheter system comprising a deployed tissue-contactor member 5 and a retracted needle electrode element means 9. The outer diameter of the deployed tissue-contactor member 5 is optionally larger than the outer diameter of the catheter shaft 1 so that the outer rim 12 of the deployed tissue-contactor member may stably stay on the inner wall of the annular organ structure. A supporting member 21 along with a plurality of auxiliary supporting members 22 secured at the distal end of the supporting member 21 forms a connecting means for connecting the tissue-contactor member 5 to the tissue-contactor deployment mechanism 15 that is located on the handle 7. The supporting member 21 and its auxiliary supporting members 22 are located within the at least one lumen 14 and have suitable torque transmittable property and adequate rigidity for deploying the tissue-contactor member 5.

The needle electrode of the first embodiment is preferably made of conductive material, while the surfaces of the catheter shaft 1, conducting wires 62, the supporting member 21 along with its auxiliary supporting members 22, are preferably covered/coated with an insulating material or electrically insulated.

In one embodiment, the needle electrode is hollow with a fluid conduit connected to an external fluid source having a fluid injection mechanism. By "fluid" is meant an injectable shapeable biomaterial that is formulated for in vivo administration by injection via a delivery system at a site of the valvular annulus defect or tissue defect. By "tissue defect" is meant vulnerable plaque, calcified tissue, valvular annulus defect, annular defect, or other lesions of atherosclerosis.

FIG. 12 shows a front cross-sectional view; section I-I of FIG. 11, of the distal tip section of a catheter system comprising a deployed tissue-contactor member 5. The tissue contactor member of the present invention in different improved embodiments adapted for serving the same indications of repairing tissue of an annular organ structure may comprise a plurality of open channels 24, pores and the like for a fluid or blood to pass from a proximal end of the tissue-contactor member to a distal end of the tissue-contactor member. The open channels may include macropores, micropores, openings, or combination thereof.

Figure 13:
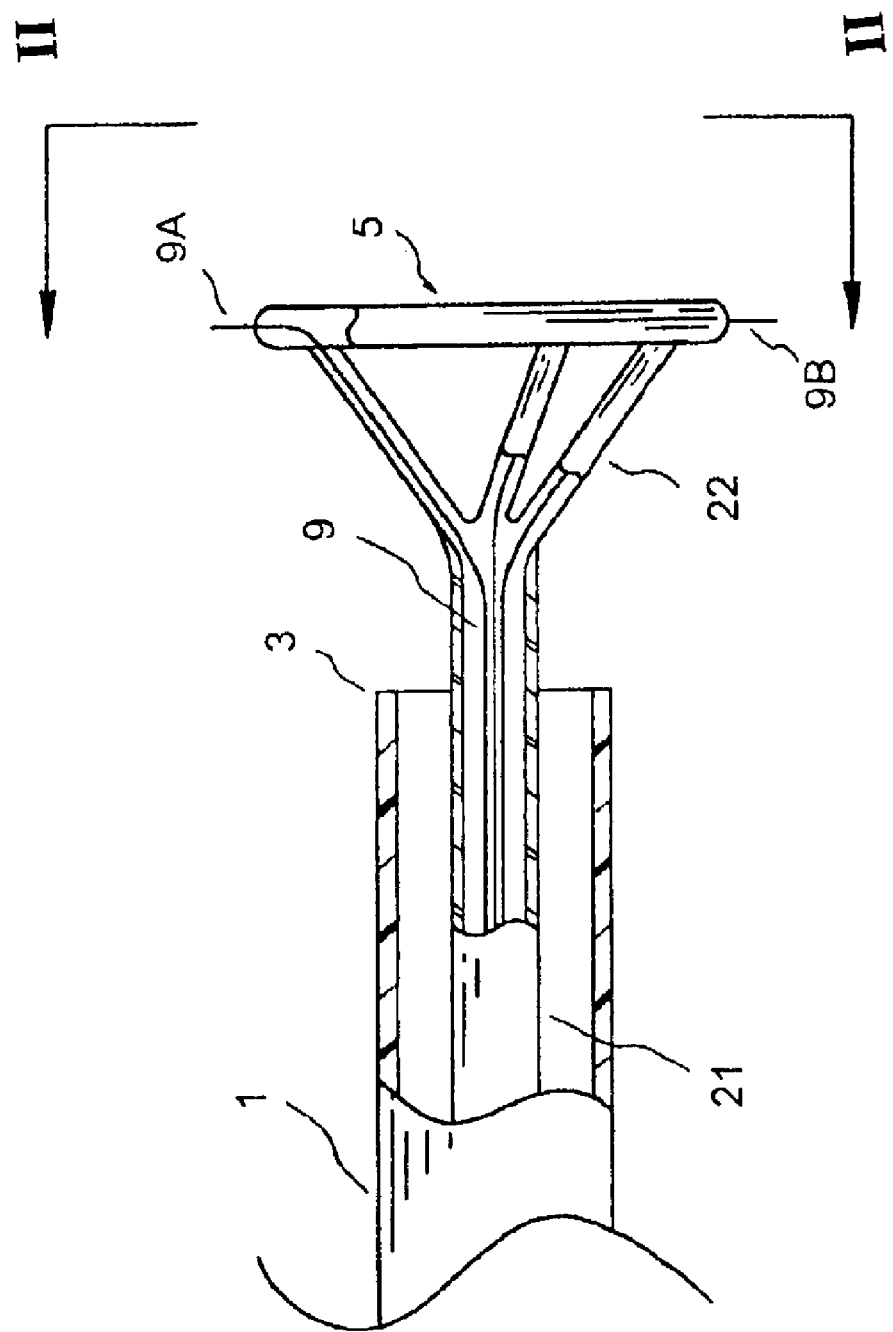
FIG. 13 is a close up view of the distal tip section of the catheter system comprising a deployed tissue-contactor-member and a deployed electrode element means at a fully deployed state.

FIG. 13 shows a close up view of the distal tip section 2 of one embodiment of the current catheter system comprising a deployed tissue-contactor member 5 and a deployed needle electrode elements 9A, 9B at a fully deployed state. The fully deployed state is used for delivery of high frequency current energy to the needle electrode elements 9A, 9B and subsequently to the site specific contact tissue for repairing the annular organ structure. The delivery of high frequency current to each of the needle electrode elements may go through a splitter or other mechanism. The needle electrode element means 9 is preformed so that when deployed, the needle electrodes are in a manner essentially perpendicular to a longitudinal axis of the catheter shaft 1 or at a suitable angle for effective thermal therapy.

Figure 14:
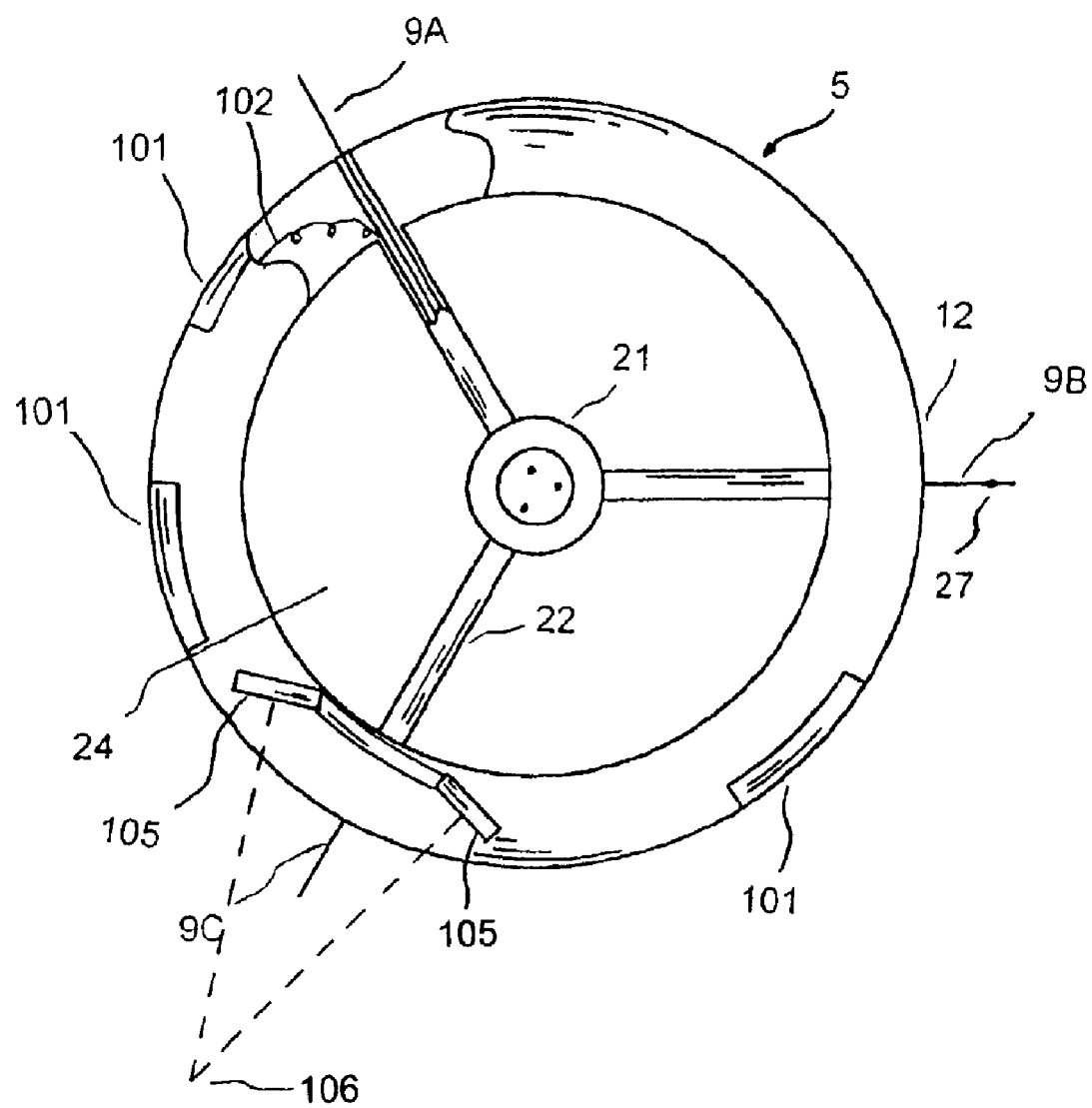
FIG. 14 is a front cross-sectional view, section II-II of FIG. 13, of the distal tip section of a catheter system comprising a deployed tissue-contactor member with a deployed electrode element means.

FIG. 14 shows a front cross-sectional view; section II-II of FIG. 13, of the distal tip section 2 of a catheter system comprising a deployed tissue-contactor member 5 and a deployed needle electrode element means 9. The tips of the needle electrodes 9A, 9B, and 9C extend out of the rim 12 of the tissue-contactor member 5 and penetrate into tissue for energy delivery.

In some particular aspect of the present invention, the deployable tissue-contactor member 5 may have a deployable needle for anchoring purposes. The deployable anchoring needle may look similar to the needle electrode element means 9 of FIG. 14 without connecting to a power source. The tissue-shrinkable energy is in term provided by strip electrodes 101 or focused ultrasound arrangement 105. The focused ultrasound arrangement 105 may be pre-mounted onto a tissue-contactor member of the present invention configured to provide focused ultrasound energy to a target tissue 106 at a pre-determined distance. The strip electrode 101 is generally mounted on the tissue contacting side of the tissue-contactor member 5, wherein the high frequency energy is transmitted through the electric conductor 102.

Figure 15:
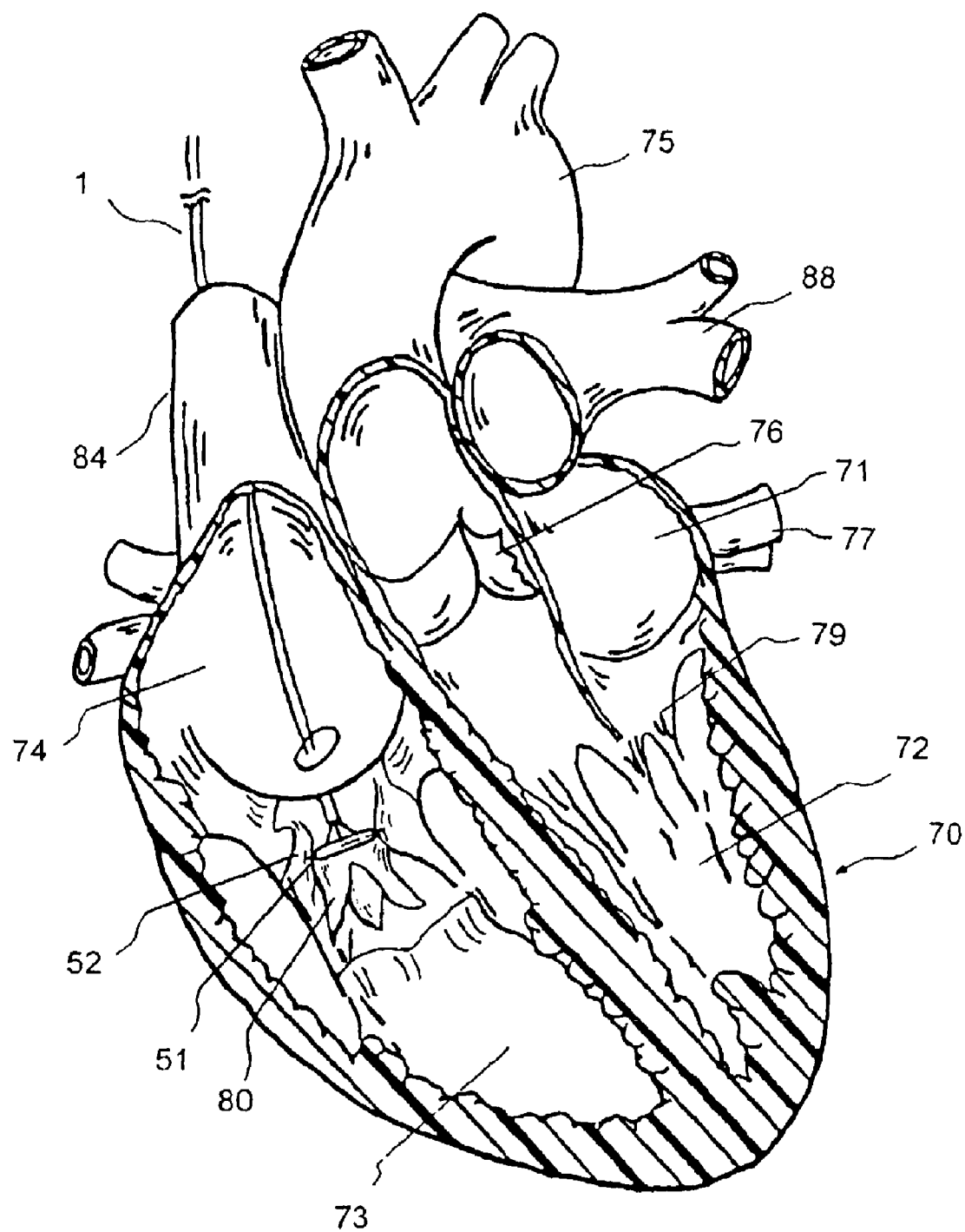
FIG. 15 is a simulated view of the catheter system of the present invention in contact with the tissue of an annular organ structure.

FIG. 15 shows a simulated view of the catheter system of the present invention in contact with the tissue 51 of an annular organ structure 52. The heart 70 has a left atrium 71, a left ventricle 72, a right ventricle 73, and a right atrium 74. The aorta 75 connects with the left ventricle 72 and contains an aorta valve 76. The pulmonary artery 77 connects with the right ventricle 73 through a pulmonary valve. The left atrium 71 communicates with the left ventricle 72 through a mitral valve 79. The right atrium 74 communicates with the right ventricle 73 through a tricuspid valve 80. Oxygenated blood is returned to the heat 70 via pulmonary veins 88. In a perspective illustration, a catheter is inserted into the right atrium 74 and is positioned on the inner wall 51 of the tricuspid valve 80. The leaflets of the tricuspid valve 80 open toward the ventricle side. Blood returned from the superior vena cava 84 and the opposite inferior vena cava flows into the right atrium 74, Subsequently, blood flows from the right atrium 74 to the right ventricle 73 through the tricuspid valve 80. Therefore, the tissue-contactor member 5 of the catheter shaft 1 does not interfere with the leaflet movement during the proposed less invasive thermal therapy of the invention.

Figure 16:
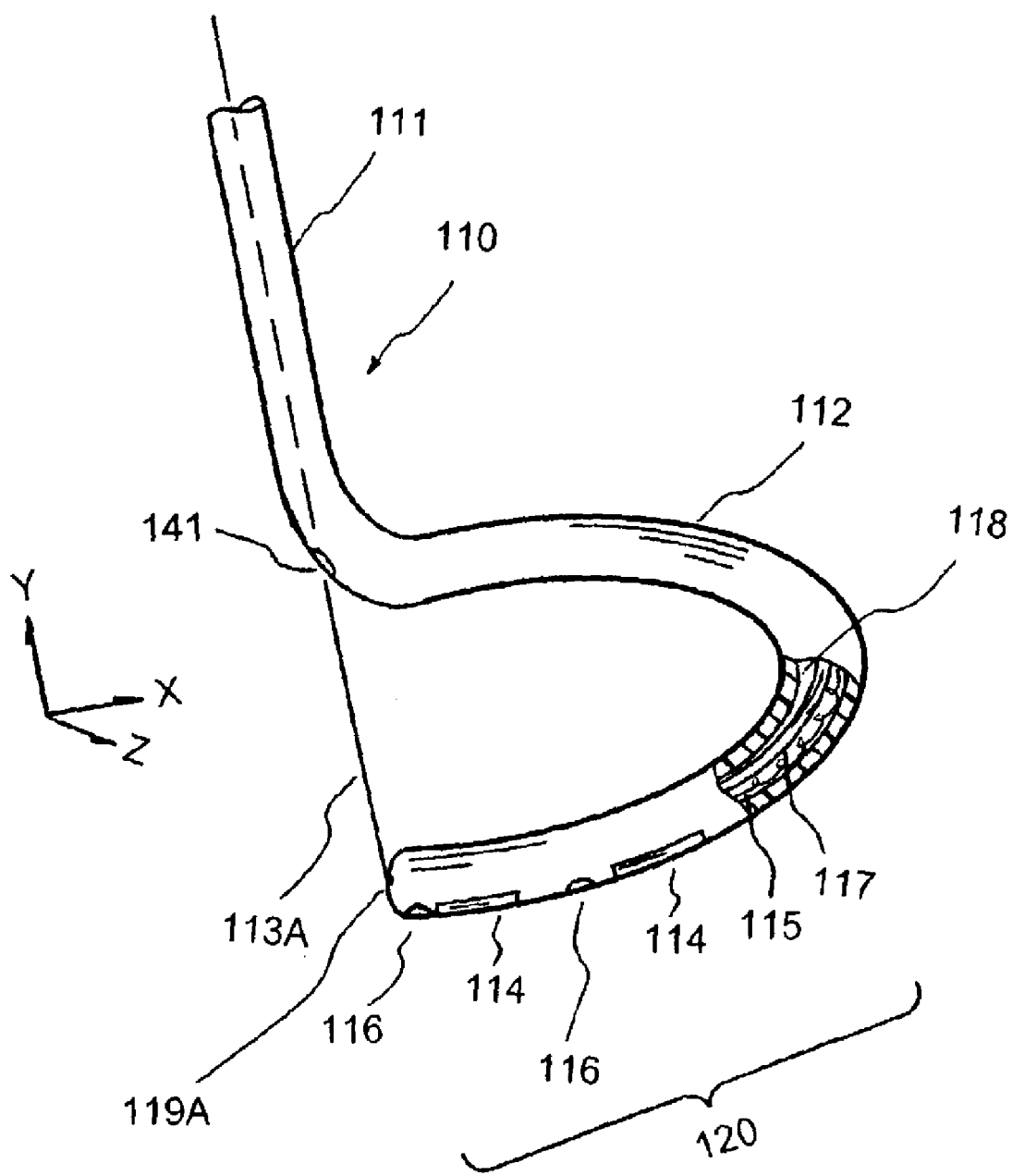
FIG. 16 illustrates an exemplary embodiment of a tissue-contactor member in accordance with the principles of the present invention.

FIG. 16 shows one aspect of the tissue-contactor member 110 of the present invention, illustrating an expandable member with suction capability. A vacuum-assisted device for maintaining the device intimately close to a tissue has been disclosed elsewhere. Bjerken in U.S. Pat. No. 6,464,707, entire contents of which are incorporated herein by reference, discloses a tube device for suturing tissue, wherein when the tube is properly positioned, a vacuum source is placed in fluid communication with the bore of the tube so that the tissue is drawn into the suction opening of the tube for placing sutures in the tissue efficiently at the surgical site.

The tissue-contactor member 110 comprises a proximal section 111 connected to a semi-circular or C-shaped end unit 112 that has a plurality of strip electrode elements 116 located at the outer tissue contacting surface of the end unit 112. The strip electrodes 116 are connected to an outside high frequency generator through an electrical conductor 115. In one preferred aspect, the proximal section 111 is along the Y-axis while the end unit 112 lies in an X-Z plane about perpendicular to the Y-axis. The member 110 also comprises a pulling cable 113A through an opening 141 at the proximal section of the end-unit 112 with one end secured to a distal end point 119A of the end unit 112 configured for forming a desired C-shape with various radius. At least a suction port 116 is located at the distal section 120 of the end unit 112, wherein the fluid communication to a vacuum source is provided. The fluid communication passageway 117 and the electrical conductor 115 are both located within a lumen 118 of the tissue-contactor member 110.

Figure 17:
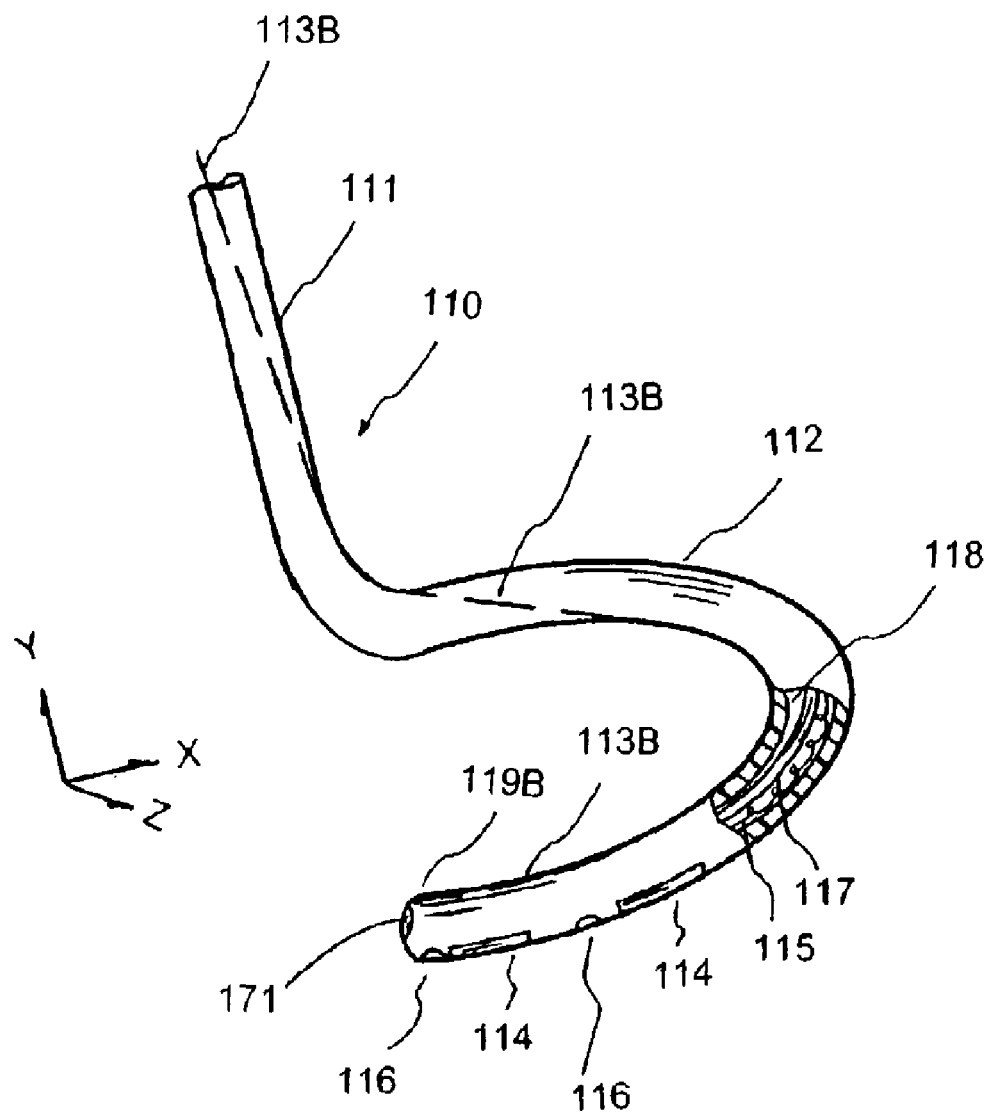
FIG. 17 illustrates an exemplary embodiment of a tissue-contactor member in accordance with the principles of the present invention.

FIG. 17 shows another aspect of the tissue-contactor member 110 of the present invention, wherein the tissue-contactor member is radially expandable for intimate tissue contact. In one aspect, the tissue-contactor member 110 comprises a proximal section 111 connected to a semi-circular or C-shaped end unit 112 that has a plurality of strip electrode elements 116 located at the outer tissue contacting surface of the end unit 112. The strip electrodes 116 are connected to an outside high frequency generator through an electrical conductor 115. In one preferred aspect, the proximal section 111 is along the Y-axis while the end-unit 112 lies in an X-Z plane approximately perpendicular to the Y-axis. The member 110 also comprises a pulling cable 113B located within the lumen 118 of the member 110 with one end secured to a distal end point 119B of the end unit 112 configured for forming a desired C-shape with various radius. At least a suction port 116 is located at the distal section 120 of the end-unit 112, wherein the fluid communication to a vacuum source is provided. The fluid communication passageway 117 and the electrical conductor 115 are both located within a lumen 118 of the tissue-contactor member 110.

The pulling cable or wire 113A, 113B, 139 may be made of a material that has the capability of pushing and pulling the distal end of the tissue-contactor member 110 as desired. The pulling cable 113A, 113B, 139 may also be connected to a computer program that monitors the movement of the annulus and provides push/pull instructions in a coordinated fashion with the movement of the annulus or the annular organ structure.

Figure 18:
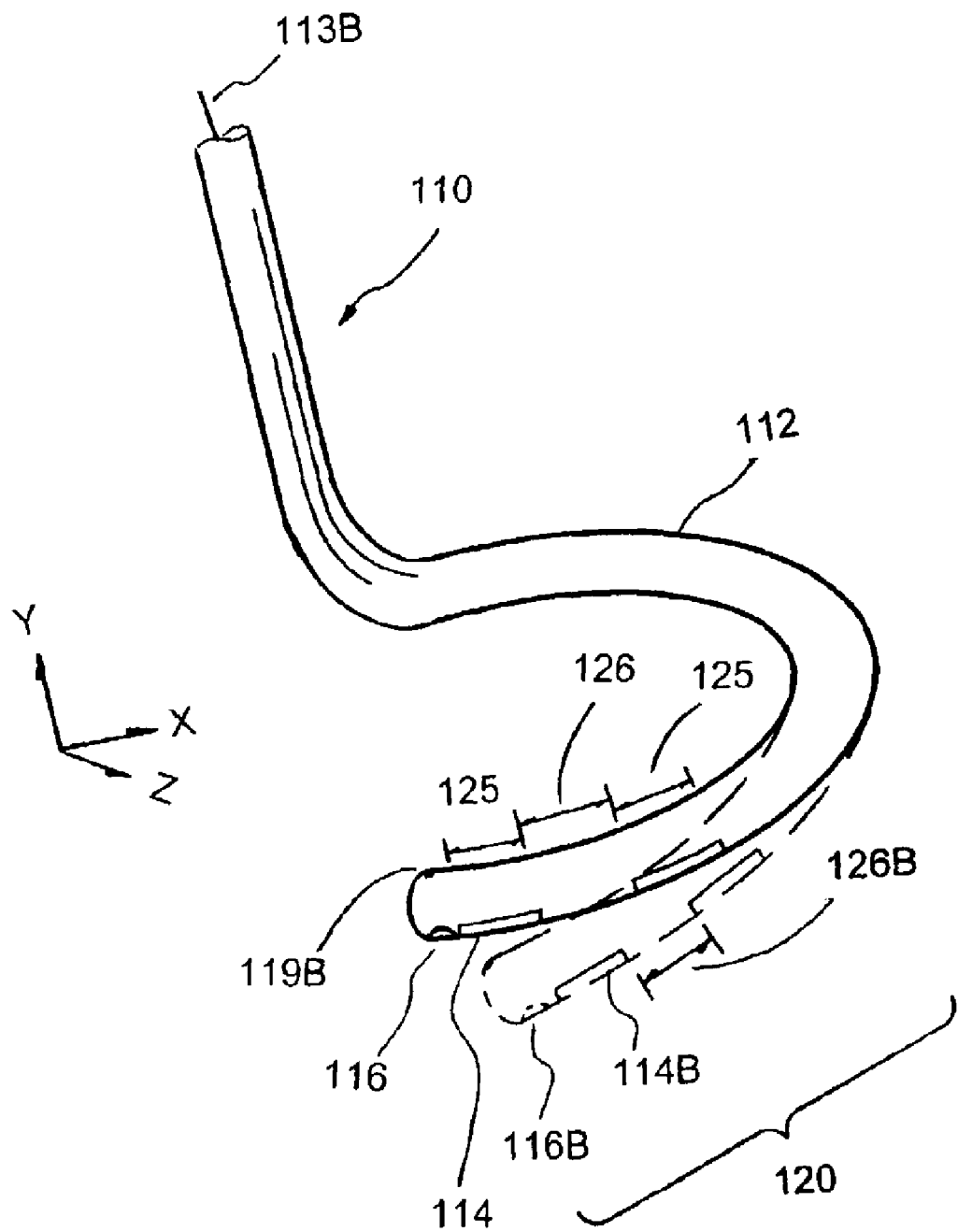
FIG. 18 illustrates an exemplary embodiment of a tissue-contactor member in accordance with the principles of the present invention.

FIG. 18 shows still another aspect of the tissue-contactor member 110 of the present invention further comprising a variable inter electrode distance to comply with beating heart movement. The end unit 112 is made of biocompatible material suitable for supporting the intended function with flexibility, in some aspects of the present invention, the end unit 112 comprises two distinct segments made of biocompatible material with different compositions. A first segment 125 is for supporting a strip electrode 114 with little longitudinal expandability and a second segment 126 located between any two strip electrode regions is made of elastic biomaterial with proper longitudinal expandability. The elastic biomaterial may be selected from the group consisting of silicone, latex, polyurethane, fluoro-elastomer, polypropylene, polyethylene, polyethylene terephthalate, nylon, and a combination thereof.

In a beating heart case, the end unit 112 is intended to move continuously along with the annulus. The annulus expands a little during its opening phase and contracts a little during its closing phase. To maintain each strip electrode at a target tissue without sliding, the inter-electrode distance may be expandable/retractable corresponding to the movement of the annulus. As illustrated in FIG. 18, the solid line distal section 120 of the end-unit 112 corresponds to an annulus-closing phase while the broken line distal section corresponds to an annulus opening phase. The inter electrode distance 126A at the annulus opening phase is longer than the inter electrode distance 126 at the annulus closing phase, while the configuration for the electrode 114B and the suction port 116B are unchanged from their annulus-closing phase, 114 and 116, respectively.

Figure 19:
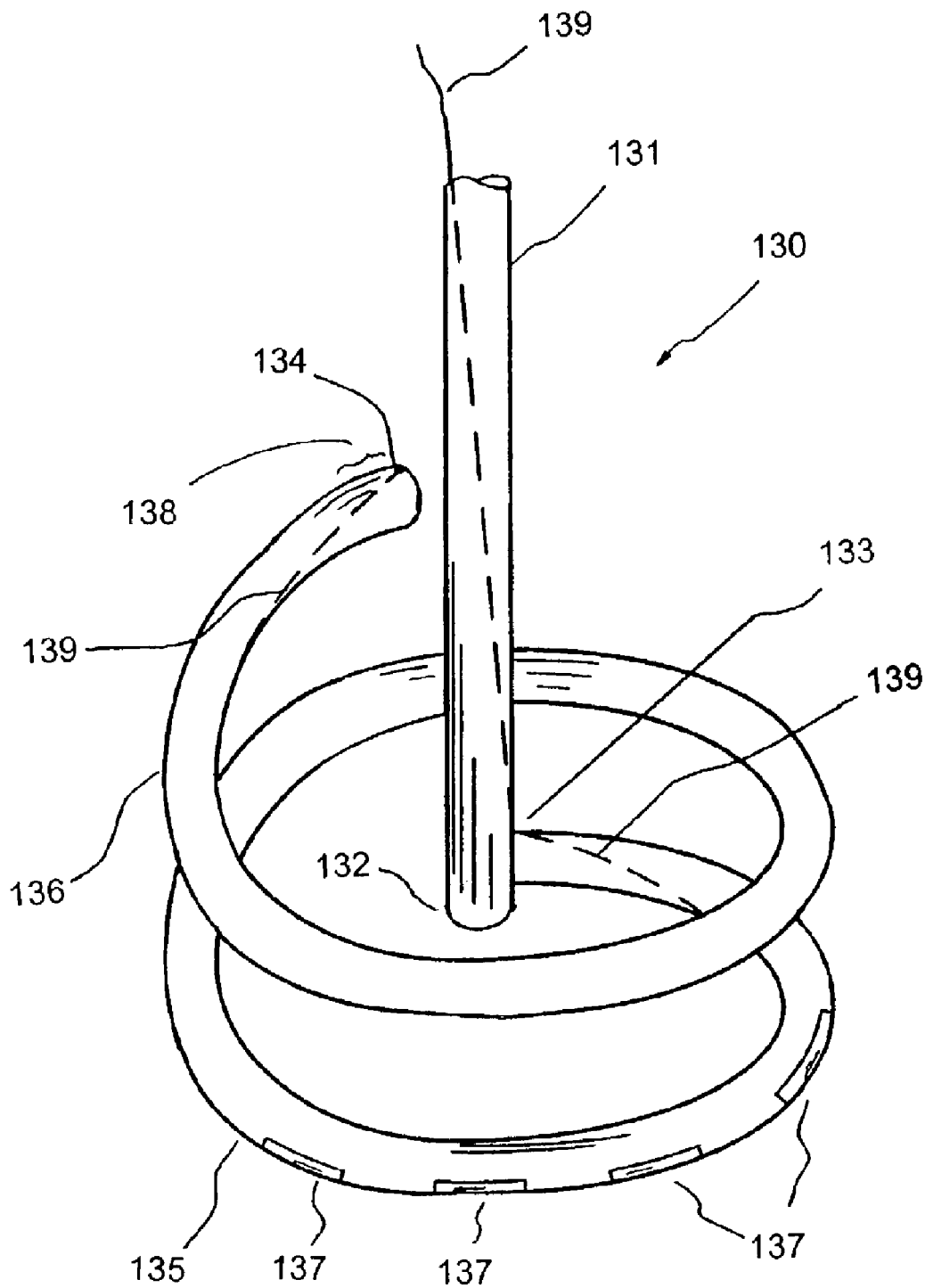
FIG. 19 illustrates an exemplary embodiment of a tissue-contactor member in accordance with the principles of the present invention.

FIG. 19 shows a further aspect of the tissue-contactor member 130 of the present invention attached at the end section 133 close to the distal end 132 of a catheter, a handheld apparatus or cannula 131, illustrating the radially moveable capability in synch with the beating heart movement. The tissue-contactor member 130 may comprise at least a loop (complete or partial) made of inflatable balloon material. For illustration purposes, the member 130 in one embodiment is consisted of two loops 135 and 136, with a plurality of strip electrodes 137 located properly on each loop. Each of the strip electrodes 137 generally faces outwardly for intimate tissue contact. The distal end of a pulling cable 139 is secured to the distal point 135 of the tissue-contactor member 134 at the distal region 138 of the loop 136. The loop is generally preshaped and configured to expand and contract along the annulus in synch with or in a coordinated fashion with the beating heart movement.

Therefore, it is one aspect of the invention to provide a method for operating a catheter system for repairing an annular organ structure of a patient, comprising: intimately contacting the annular organ structure by a tissue-contactor member having energy-delivering elements; and delivering tissue-shrinkable energy at the annular organ structure through the elements, wherein the tissue-shrinkable energy is applied at a distance wirelessly from the elements sufficient to shrink and tighten the organ structure. In some embodiment, the tissue-shrinkable energy is infrared energy, ultrasound energy, focused ultrasound energy, and the tissue-shrinkable energy is provided noninvasively from outside a body of the patient. In one embodiment, the elements move in a coordinated fashion with movement of the annulus. The step of intimately contacting the annulus may be carried out by at least a suction port provided on the tissue-contactor member or by at least a needle mounted on the tissue-contactor member for penetrating into tissue of the annulus. The high frequency energy may be focused ultrasound energy, radiofrequency energy, microwave energy, electromagnetic energy, laser energy, or the like. The annular organ structure is selected from the group consisting of a mitral valve, a tricuspid valve, a pulmonary valve, an aortic valve, a venous valve, a sphincter or a valvular annulus.

In one embodiment, a method for operating a catheter system for repairing an annulus comprises compressively sandwiching the annulus by a tissue-contactor member having electrode elements and delivering high frequency energy at or near the annulus through the electrode elements. Further, the method for repairing an annulus having valvular leaflets further comprises delivering high frequency energy to the leaflets.

Figure 22:
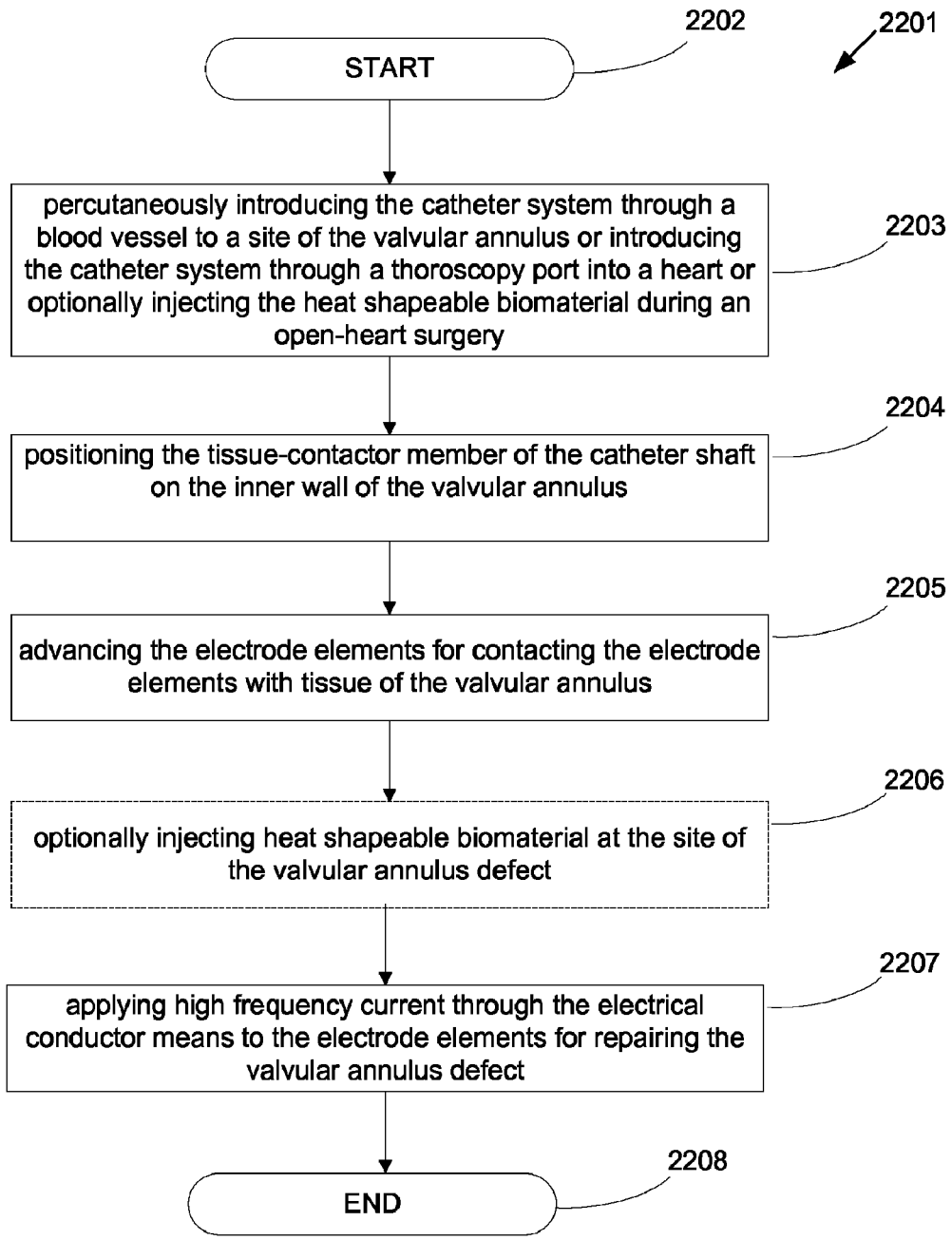
FIG. 22 illustrates a flowchart of an exemplary method for operating a catheter system.

FIG. 22 illustrates a flowchart of an exemplary method for operating a catheter system. In a embodiment, a method for operating a catheter system of the present invention for repairing a valvular annulus is shown in process 2201. Process 2201 begins at step 2202. Processing continues to step 2203: percutaneously introducing the catheter system through a blood vessel to a site of the valvular annulus or introducing the catheter system through a thoroscopy port into a heart or optionally injecting the heat shapeable biomaterial during an open-heart surgery. Processing continues to step 2204: positioning the tissue-contactor member of the catheter shaft on the inner wall of the valvular annulus. Processing continues to step 2205: advancing the electrode elements for contacting the electrode elements with tissue of the valvular annulus Processing continues to optional step 2206: optionally injecting heat shapeable biomaterial at the site of the valvular annulus defect. Processing continues to step 2207: applying high frequency current through the electrical conductor means to the electrode elements for repairing the valvular annulus defect. Processing continues to step 2208, where process 2201 terminates.

The tissue of the heart valve in the procedures may be selected from the group consisting of valvular annulus, chordae tendinae, valve leaflet, and papillary muscles The high frequency current in the procedures may be selected from the group consisting of radiofrequency current, microwave current, ultrasound current, focused ultrasound, and combination thereof.

U.S. Pat. No. 6,451,044 issued on Sep. 17, 2002, entire contents of which are incorporated herein by reference, discloses an ultrasonically heatable stent comprising at least one ultrasound-absorptive material characterized by an acoustic impedance greater than that of living soft tissue, and a method of advantageously positioning at least one ultrasound transducer external to the body of the subject; and operating the ultrasound transducer such that an ultrasonic beam is directed at the stent, whereby the temperature of the stent is maintained at about 1-5° C. above ambient temperature for a sufficient period of time to heat the region of vessel wall at a temperature of 38-42° C.

A temperature sensor 27, either a thermocouple type or a thermister type, is constructed at the proximity of at least one electrode of the present invention, for example the electrode 9B (shown in FIG. 14) to measure the tissue contact temperature when high frequency energy is delivered. A temperature sensing wire 28 from the thermocouple or thermister is connected to one of the contact pins of the connector 8 and externally connected to a transducer and to a temperature controller 29. The temperature reading is thereafter relayed to a closed-loop control mechanism to adjust the high frequency energy output. The high frequency energy delivered is thus controlled by the temperature sensor reading or by a preprogrammed control algorithm.

There is also a clinical need for an improved apparatus system having capabilities of measuring a contact force at the point of contact with the tissue to be treated. U.S. Pat. No. 6,113,593 to Tu et al, entire contents which are incorporated herein by reference, discloses a force measuring means for measuring force exerted onto the temperature sensing probe by a tissue and RF current generating means for generating RF current, wherein the RF current generating means is connected to and controlled by the temperature sensing means and force measuring means, adapted for supplying RF current to the temperature sensing probe as an electrode for tissue treatment. In some aspect of the invention, it is provided a method for operating a for repairing an annulus, comprising providing a tissue-contactor member having tissue-shrinkable energy, positioning the member at about the annulus, intimately contacting the annulus by the tissue-contactor member, and delivering energy at about the annulus though the member.

Figure 20:
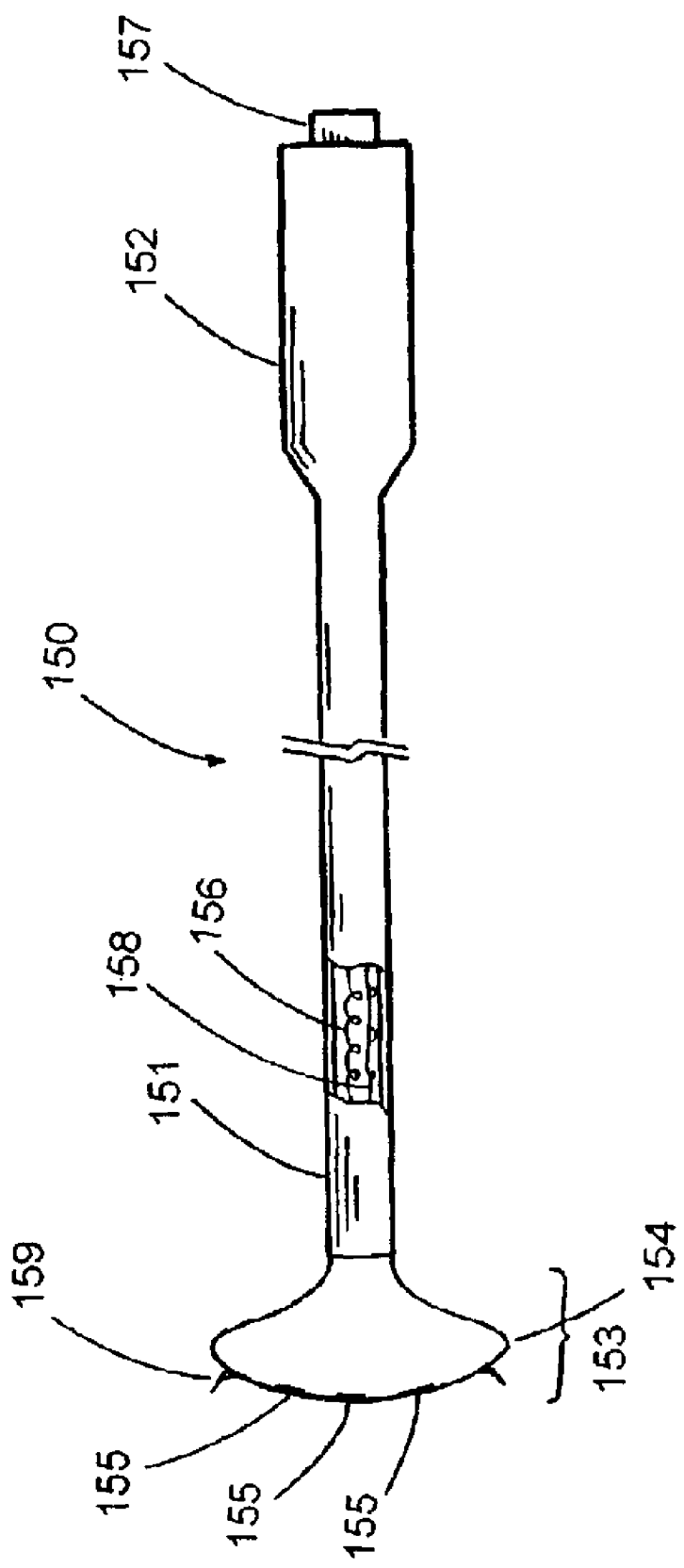
FIG. 20 illustrates an exemplary embodiment of a hand-held apparatus useful in surgical operations in accordance with the principles of the present invention.

FIG. 20 shows one embodiment of a hand-held apparatus 150 that is useful in surgical operations in accordance with the principles of the present invention. The apparatus 150 comprises a malleable body 151 that is attached to a handle 152, wherein the malleable body 151 has a tissue-contactor member 153 and a distal end 154. There provides a plurality of electrodes 155 at about the periphery of the tissue-contactor member 153. In one embodiment, the electrodes are strip electrodes or section electrodes that do not cover the whole circumference of the tissue-contactor member. The conducting wire means 156 for supplying energy to each individual electrode passes though the cavity of the malleable body 151 and the handle 152 and connects to an external power source though the end connector 157. It a embodiment, the tissue-contactor member 153 comprises means 159 for measuring a contact force at a point of the member onto the annulus though a force transmission line 158.

Figure 21:
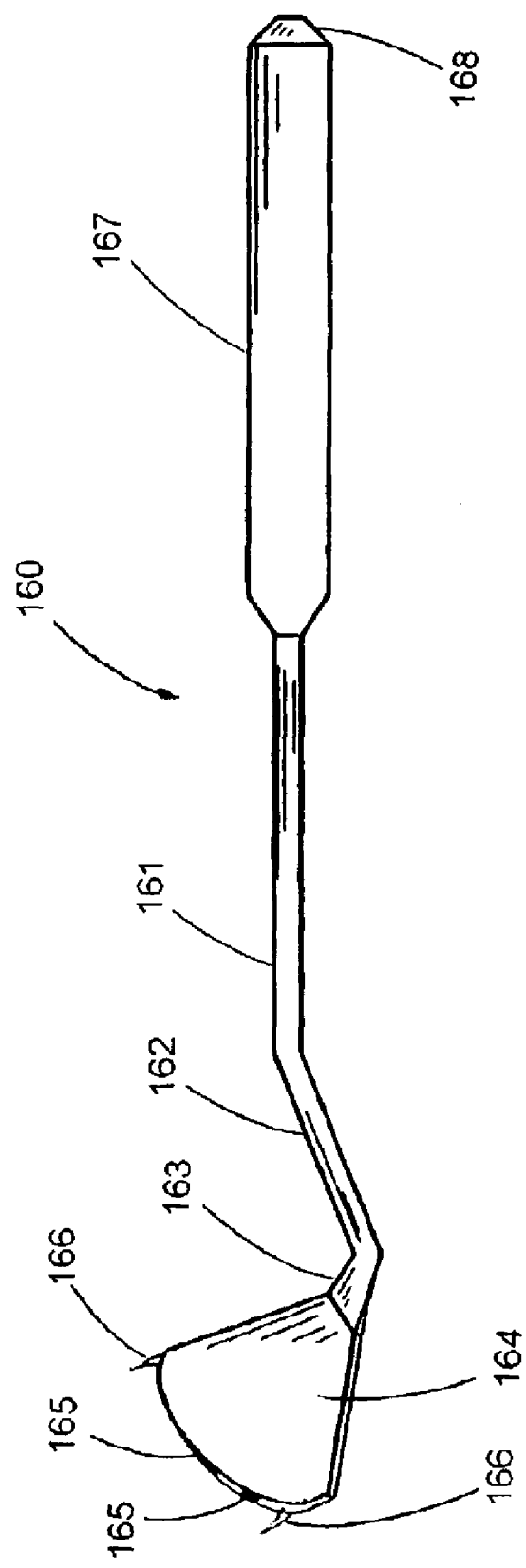
FIG. 21 illustrates an exemplary embodiment of a hand-held apparatus useful in surgical operations in accordance with the principles of the present invention.

FIG. 21 shows another embodiment of a hand-held apparatus 160 that is useful in surgical operations in accordance with the principles of the present invention. The apparatus 160 comprises at least one section 161, 162, 163 made of malleable body element and a distal tissue contactor member 164 that has a plurality of electrodes 165 at its outermost surface. The outermost surface is sized and configured to intimately contact at least a portion of the annulus. In one embodiment, there is provided means 166 for releasably anchoring the member 164 onto the annulus, the means being selected from a group consisting of needles, barbs, protrusions, and spikes. The apparatus 160 further comprises a handle 167 and end connector 168 for connecting the conductors to an external energy source.

In some aspects of the invention, a method is provided for operating a system for repairing an annulus, comprising providing a tissue-contactor member having tissue-shrinkable energy, positioning the member at about the annulus, intimately contacting the annulus by the tissue-contactor member, and delivering energy at about the annulus through the member. The energy may be cryoablation energy or radiofrequency energy.

In one embodiment, the system is a cannula or a surgical hand-held apparatus for approaching the annulus through an open chest procedure, wherein the open chest procedure is a sternotomy or a thoracotomy. In another embodiment, the cannula or surgical hand-held apparatus is malleable sized and configured for intimately contacting at least a portion of the annulus. In still another embodiment, the step of intimately contacting the annulus by the tissue-contactor member is carried out by means for releasably anchoring the member onto the annulus, the means being selected from a group consisting of needles, barbs, protrusions, and spikes.

In some aspects, the system is a catheter wherein a working distal end of the catheter is covered by a plurality of adjacent filaments which are bound together by suturing, braiding, jacketing or encapsulating to provide a non-skid surface. In a further aspect, the tissue contactor member comprises means for measuring a contact force at a point of the member onto the annulus and the tissue-contactor member comprises means for measuring impedance. In some aspects, it is provided a step of measuring impedance adapted for aiding in identification of tissue type, such as collagen-rich tissue.

In some aspects, the system comprises at least one magnet 171 mounted at about the tissue-contactor member 110 (FIG. 17) and a remote opposing magnetic energy source (not shown), the method further comprising a step of activating the opposing magnetic energy source to attractively position the tissue-contactor member by magnetically pulling force. The opposing magnetic energy source is located at a location selected from a group consisting of inside a heart chamber, on a heart surface, in a cardiac vein or outside a body.

This invention also discloses a method for repairing a valvular annulus defect, the method comprising injecting a heat shapeable biomaterial formulated for in vivo administration by injection via a catheter system at a site of the valvular annulus defect; and applying heat sufficient to shape the biomaterial and immobilize the biomaterial at about the annulus defect.

The term "shapeable biomaterial" as used herein is intended to mean any biocompatible material that changes its shape, size, or configuration at an elevated temperature without significantly affecting its composition or structure. The shaping of a shapeable biomaterial is usually accomplished by applying moderate energy. For example, a crosslinked material is structurally different from a non-crosslinked counterpart and is not considered as a shaped material. The elevated temperature in this invention may range from about 39° C. to about 45° or higher, wherein the heat is below a temperature for effecting crosslinking of the biomaterial.

The biomaterial may comprise a matrix of collagen, a connective tissue protein comprising naturally secreted extracellular matrix, a heat shapeable polymer, or the like.

The term "matrix of collagen" as used herein is intended to mean any collagen that is injectable through a suitable applicator, such as a catheter, a cannula, a needle, a syringe, or a tubular apparatus. The matrix of collagen as a shapeable biomaterial of the present invention may comprise collagen in a form of liquid, colloid, semi-solid, suspended particulate, gel, paste, combination thereof, and the like. Devore in PCT WO 00/47130 discloses injectable collagen-based system defining matrix of collagen, entire disclosure of which is incorporated herein by reference.

The shapeable biomaterial may further comprise a pharmaceutically acceptable carrier for treating the annulus defect and a drug is loaded with the pharmaceutically acceptable carrier, wherein the drug is selected from a group consisting of an anti-clotting agent, an anti-inflammatory agent, an anti virus agent, an antibiotic, a tissue growth factor, an anesthetic agent, a regulator of angiogenesis, a steroid, and combination thereof.

The connective tissue protein comprising naturally secreted extracellular matrix as a shapeable biomaterial of the present invention may be biodegradable and has the ability to promote connective tissue deposition, angiogenesis, and fibroplasia for repairing a tissue defect. U.S. Pat. No. 6,284,284 to Naughton discloses compositions for the repair of skin defects using natural human extracellular matrix by injection, entire contents of which are incorporated herein by reference. Bandman et al. in U.S. Pat. No. 6,303,765 discloses human extracellular matrix protein and polynucleotides, which identify and encode the matrix protein, wherein the human extracellular matrix protein and its polynucleotides may form a shapeable biomaterial of the present invention.

The shapeable polymer as a biomaterial in the present invention may also comprise biodegradable polymer and non-biodegradable polymer, including prepolymer and polymer suspension. In one embodiment, the shapeable polymer in this invention may be selected from a group consisting of silicone, polyurethane, polyamide; polyester, polystyrene, polypropylene, polyacrylate, polyvinyl, polycarbonate, polytetrafluoroethylene, poly (1-lactic acid), poly (d, 1-lactide glycolide) copolymer, poly (orthoester), polycaprolactone, poly (hydroxybutyrate/hydroxyvaleerate) copolymer, nitrocellulose compound, polyglycolic acid, cellulose, gelatin, dextran, and combination thereof.

Slepian et al. in U.S. Pat. No. 5,947,977 discloses a novel process for paving or sealing the interior surface of a tissue lumen by entering the interior of the tissue lumen and applying a polymer to the interior surface of the tissue lumen. Slepian et al. further discloses that the polymer can be delivered to the lumen as a monomer or prepolymer solution, or as an at least partially preformed layer on an expansible member, the entire contents of which are incorporated herein by reference. The polymer as disclosed may be suitable as a component of the shapeable biomaterial of the present invention.

A method for joining or restructuring tissue consisting of providing a preformed sheet or film which fuses to tissue upon the application of energy is disclosed in U.S. Pat. No. 5,669,934, entire contents of which are incorporated herein by reference. Thus, the protein elements of the tissue and the collagen filler material can be melted or denatured, mixed or combined, fused and then cooled to form a weld joint. However, the heat shapeable biomaterial of the present invention may comprise collagen matrix configured and adapted for in vivo administration by injection via a catheter system at a site of the tissue defect; and applying heat sufficient to shape the biomaterial and immobilize the biomaterial at about the tissue defect, but not to weld the tissue.

An injectable bulking agent composed of microspheres of crosslinked dextran suspended in a carrier gel of stabilized hyaluronic acid is marketed by Q-Med AB (Uppsala, Sweden). In one embodiment of applications, this dextran product may be injected submucosally in the urinary bladder in close proximity to the ureteral orifice. The injection of dextran creates increased tissue bulk, thereby providing coaptation of the distal ureter during filling and contraction of the bladder. The dextran microspheres are gradually surrounded by body's own connective tissue, which provides the final bulking effect. The heat shapeable polymer of the present invention may comprise dextran configured and adapted for in vivo administration by injection via a catheter system at a site of the tissue defect; and applying heat sufficient to shape the biomaterial and immobilize the biomaterial at about the tissue defect.

Sinofsky et al. in U.S. Pat. No. 5,100,429 discloses an uncured or partially cured, collagen-based material delivered to a selected site in a blood vessel and is crosslinked to form an endoluminal stent, entire contents of which are incorporated herein by reference. The collagen based material as disclosed may form a component of the shapeable biomaterial of the present invention.

Edwards in PCT WO 01/52930 discloses a method and system for shrinking dilatations of a body, removing excess, weak or diseased tissues and strengthening remaining tissue of the lumen walls, the entire contents of which are incorporated herein by reference. However, Edwards does not disclose a method for repairing a tissue defect comprising: injecting a heat shapeable biomaterial formulated for in vivo administration by injection via a percutaneous delivery system at a site of the tissue defect; and applying heat to the biomaterial and a portion of the tissue defect adapted for shaping the biomaterial, the heat being below a temperature sufficient for effecting crosslinking of the biomaterial and the portion of the tissue defect.

Therefore, it is a further embodiment to provide a method for repairing a tissue defect comprising: injecting a heat shapeable biomaterial formulated for in vivo administration by injection via a percutaneous delivery system at a site of the tissue defect; and applying heat to the biomaterial and a portion of the tissue defect adapted for shaping the biomaterial, the heat being below a temperature sufficient for effecting crosslinking of the biomaterial and the portion of the tissue defect, the tissue defect may comprise vulnerable plaque, calcified tissue, or other lesions of atherosclerosis.

From the foregoing, it should now be appreciated that an improved catheter system and methods having electrode element means and high frequency current energy intended for tightening and stabilizing the tissue of an annular organ structure has been disclosed. It is generally applicable for repairing an annular organ structure of a heart valve, an annular organ structure of a venous valve, a valve leaflet, chordae tendinae, papillary muscles, and the like. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

While the invention herein disclosed has been described by means of specific embodiments and applications thereof, numerous modifications and variations could be made thereto by those skilled in the art without departing from the scope of the invention set forth in the claims.

What is claimed is:

1. A method for operating a system to tighten and stabilize a target zone of a collagenous tissue within a patient's body, comprising the steps of:
    providing a device configured to deliver tissue-shrinkable energy to a target zone comprising an annular organ structure of a heart valve within a patient's body via a catheter comprising a flexible tissue contactor member comprising energy-delivering elements, wherein said flexible tissue contactor member is configured to compressively confine an inner wall of said annular organ structure between a distal end of said flexible tissue contactor member and a proximal end of said flexible tissue contactor member, and wherein said flexible tissue contactor member is located at a distal tip of said catheter and inside at least one lumen of said catheter extending between said distal tip and a proximal end where said flexible tissue contactor member is deployed out of said at least one lumen;
    introducing said catheter through to a site of said annulus;
    deploying said flexible tissue-contactor member;
    positioning said tissue-contactor member to compressively confine said inner wall of said annulus;
    advancing said energy-delivering elements to contact tissue of said annulus; and,
    delivering a tissue-shrinkable energy to said target zone wirelessly, wherein said tissue-shrinkable energy is provided noninvasively from outside a body of the patient, wherein said tissue-shrinkable energy is sufficient to shrink and tighten said annular organ structure.

2. The method of claim 1, wherein said annular organ structure is selected from a group consisting of a mitral valve, a tricuspid valve, a pulmonary valve, an aortic valve, and a venous valve.

3. The method of claim 1, wherein said annular organ structure is a sphincter annulus or a valvular annulus.

4. The method of claim 1, wherein said tissue-shrinkable energy is selected from a group consisting of, radiofrequency energy, and microwave energy, and any combination thereof.

5. The method of claim 1, wherein said tissue-shrinkable energy is ultrasound energy.

6. The method of claim 1, wherein said flexible tissue-contactor member comprises a means for releasably anchoring onto the annulus of said target zone.

7. The method of claim 1, wherein said distal end of said flexible tissue contactor member and said proximal end of said flexible tissue contactor member are radially enlarged.

8. The method of claim 1, wherein said flexible tissue contactor member comprises an inflatable balloon comprising a radially enlarged proximal region, a middle region, and a radially enlarged distal region, said method further comprising the step of:
providing a liquid in fluid communication with said flexible tissue contactor member to inflate said flexible tissue contactor member.

9. The method of claim 1, wherein said flexible tissue contactor member comprises a hyperbolic shape with a neck region adapted for positioning said neck region at about said inner wall of said annular organ structure, wherein said plurality of energy-delivering elements are positioned about said neck region, said method further comprising the step of:
positioning said neck region at about said inner wall of said annular organ structure.

10. The method of claim 1, wherein said flexible tissue contactor member comprises a portion on a Y axis and a C-shaped end unit in an X-Z plane approximately perpendicular to said Y axis, wherein said plurality of energy-delivering elements are located on an outer tissue-contacting surface of said C-shaped end-unit, wherein a segment between at least two of said plurality of energy-delivering elements comprises elastic biomaterial with longitudinal expandability, said method further comprising the step of:
positioning said elastic biomaterial to expand and contract along said annular organ structure in synch with a natural movement of said annular organ structure.

11. A method for operating a system to tighten and stabilize a target zone of a collagenous tissue within a patient's body, comprising the steps of:
providing a device configured to deliver tissue-shrinkable energy to a target zone comprising an annular organ structure of a heart valve within a patient's body via a flexible tissue contactor member comprising energy-delivering elements, wherein said flexible tissue contactor member is configured to compressively confine an inner wall of said annular organ structure between a distal end of said flexible tissue contactor member and a proximal end of said flexible tissue contactor member;
introducing said catheter through to a site of said annulus;
deploying said flexible tissue-contactor member;
positioning said tissue-contactor member to compressively confine said inner wall of said annulus;
advancing said energy-delivering elements to contact tissue of said annulus;
delivering a heat-shapeable biomaterial at said target zone; and
delivering a tissue-shrinkable energy to said target zone wirelessly through said energy-delivering elements located outside said patient's body, wherein said tissue-shrinkable energy is provided noninvasively from outside a body of the patient, wherein said tissue-shrinkable energy is sufficient to shrink and tighten said annular organ structure.

12. The method of claim 11 further comprising the steps of:
immobilizing said heat-shapeable biomaterial at about said target zone.

* * * * *